United States Patent
Edge et al.

(10) Patent No.: US 6,521,448 B1
(45) Date of Patent: Feb. 18, 2003

(54) PORCINE MHC CLASS I GENES AND USES THEREOF

(75) Inventors: Albert S. B. Edge, Cambridge, MA (US); Henry F. Oettinger, Waban, MA (US)

(73) Assignee: Diacrin, Inc., Charlestown, MA (US)

( * ) Notice: Subject to any disclaimer, the term of this patent is extended or adjusted under 35 U.S.C. 154(b) by 0 days.

(21) Appl. No.: 08/914,372

(22) Filed: Aug. 19, 1997

(51) Int. Cl.$^7$ .................. C12N 15/12; C12N 15/63; C12N 15/74; C12N 15/79

(52) U.S. Cl. ................. 435/320.1; 435/325; 435/410; 435/243; 536/23.1; 536/23.5

(58) Field of Search .................. 536/23.1, 23.5; 435/320.1, 325, 410, 243

(56) References Cited

U.S. PATENT DOCUMENTS 5,283,058 A    2/1994  Faustman ................ 424/152.1

FOREIGN PATENT DOCUMENTS

| WO | WO 93/09815 | 5/1993 |
| WO | WO 94/26289 | 11/1994 |
| WO | WO 95/21527 | 8/1995 |

OTHER PUBLICATIONS

Sullivan, J. et al., J. Immunol. 159:2318–26, Analysis of polymorphism in porcine MHC Class I genes. Sep. 1, 1997.*
Biassoni et al., "Amino Acid Substitutions Can Influence the Natural Killer . . . NK Clones," J. Exp. Med. (1995) 182:605.
Cella et al., "NK3–specific Natural Killer Cells are Selectively Inhibited by Bw4–positive HLA Alleles with Isoleucine 80," (1994) J. Exp. Mec. 180: 1235.
Colonna et al., "HLA–C is the inhibitory ligand that determines dominant resistance to lysis bl NK1– and NK2–specific natural killer cells," (1993) Proc. Natl. Acad. Sci. USA 90:12000.
Dohring et al., "A Human Killer Inhibitory Receptor Specific for HLA–A," (1996) J. Immunol. 156:3098.
Donnelly et al., "Human Natural Killer Cells Account for Non–MHC Class 1–Restricted Cytolysis of Porcine Cells," (1997) Cell. Immunol. 175:171.
Gumperz et al., "The Bw4 Public Epitope of HLA–B Molecules Confers Reactivity with Natural Killer Cell Clones that Express NKB1, A Putative HLA Receptor," (1995) J. Exp. Med. 181:1133.
Kaufman and Ildstad, "Induction of donor–specific tolerance by transplantation of bone marrow," (1994) Therapeutic Immunol. 1:101.
Lanier, "Natural Killer Cells: From No Receptors to Too Many," (1997) Immunity 6:371.
Mandelboim et al., "Protection from Lysis by Natural Killer Cells of Group 1 and 2 Specificity is Mediated by Residue 80 in Human Histocompatibility . . . Molecules," (1996) J. Exp. Med. 184:913.
Murray et al., "Porcine Aortic Endothelial Cells Activate Human T Cells: Direct Presentation of MHC Antigens and Costimulation by Ligands for Human CD2 and CD28," (1994) Immunity 1:57.
Parham et al., "The Origins of HLA–A,B,C Polymorphism," (1995) Immunol. Rev. 143:141.
Parham et al., "Nature of polymorphism in HLA–A, –B, and –C molecules," (1988) Proc. Natl. Acad. Sci. USA 85:4005.
Pazmany et al., "Protection from Natural Killer Cell–Mediated Lysis by HLA–G Expression on Target Cells," (1996) Science 274:792.
Rollins et al., "Evidence that Activation of Human T Cells by Porcine Endothelium Involves Direct Recognition of Porcine . . . and CD2," (1994) Transplantation 57:1709.
Salter et al., "A binding site for the T–cell co–receptor CD8 . . . HLA–A2," (1990) Nature 345:41.
Satz et al., "Structure and Expression of two Porcine Genomic Clones Encoding Class I MHC Antigens," (1985) J. Immunol. 135:2167.
Shafer et al., "Expression of a swine class II gene in murine bone marrow hematopoietic cells by retroviral–mediated gene transfer," (1991) Proc. Natl. Acad. Sci. USA 88:9760.
Singer et al., "Characterization of a porcine genomic clone encoding a major histocompatibility antigen: Expression in mouse L cells," (1982) Proc. Natl. Acad. Sci. USA 79: 1403.
Singer et al., "Structure and Expression of Class 1 MHC Genes in the Miniature Swine," (1987) Veterinary Immunology and Immunopathology 17:211.
Storkus et al., "Class I–induced resistance to natural killing: Identification of nonpermissive residues in HLA–A2," Proc. Natl. Acad. Sci. USA 88:5989.
Yamada et al., "Human Anti–Porcine Xenogeneic T Cell Response," (1995) J. Immunol. 155:5249.

* cited by examiner

Primary Examiner—Ronald B. Schwadron
(74) Attorney, Agent, or Firm—Fish & Richardson P.C.

(57) ABSTRACT

The invention features porcine MHC class I genes and the use of the polypeptides they encode in induction of graft-specific immunological tolerance in recipients of porcine cell or organ transplant and the generation of certain useful antibodies.

5 Claims, 12 Drawing Sheets

```
     ATGGGGCCTGGAGCCCTCTTCCTGCTGCTGTCGGGGACCCTGGCCCTGACCGGGACCCAGGCGGGTCCCCACTCCCTGAGCTATTTCTAC MAJORITY
1    .......................................................................................... PA1
1    ..................................T..T....G..A...................G......G.. PC1
1    .......................................................................................... PD1

ACCGCCGTGTCCCGGCCCGACCGCGGGGAGCCCCGXTTCATCGCCGTCGGCTACGTGGACGACACGCAGTTCGTGCGGTTCGACAACTAC
91   ............................CG............................................................
91   .................A..A.......T......T...............................................G.G..
91   ................CT.T..C....................................................................

GCCCCGAATCCGCGGATGGAGCCTCGGGTGCCGTGGATACAGCAGGAGGGGCAGGAGTATTGGGATGAGGAGACGCGGAAXGTCAAGGAC
181  ...................................................C.....................A................
181  .....C............G....C..............A...........................A...C.C..T..G.
181  ..................................................CG...............T........A

AXCGCACAGACTTTCCGAGTGGGCCTGAACACCCTGCGCGGCTACTACAACCAGAGCGAGGCCGGGTCTCACACCCTCCAGAGCATGTAC
271  .A........C............................................................................TT
271  .G............AA......G.A..................................................................
271  .C......A.G................................................................................

GGCTGCTACTTGGGACCAGACGGGCTCCTCCTCCACGGGTACAGACAGGACGCCTACGACGGCGCCGATTACATCGCCCTGAACGAGGAC
361  ............................................................................................
361  ......G..G............T......G.......CAT...................................................
361  ............................................................................................

CTGCGCTCCTGGACCGCGGCGGACATGGCGGCTCAGATCXCCAAGCGCAAGTGGGAGGCGGCCGATGAGGCGGAGCGGAGGAGGAGCTAC
451  ..................................T.......................................T................
451  ................C..............G.....................T....T...A.T..........................
451  ....................................A............................T.........................

CTGCAGGGCCXGTGTGTGGAGTGGCTCCGCAGATACCTGGAGATGGGGAAGGACACGCTGCAGCGCGCAGAGCCTCCAAAGACACATGTG
541  .........G.........G.........C..........................................C..................
541  ...G.....GC.........AG.A..........A..TA....................................................
541  .......A.T..........C.......................................................................

ACCCGCCACCCCAGCTCTGACCTGGGGGTCACCTTGAGGTGCTGGGCCCTGGGCTTCTACCCTAAGGAGATCTCCCTGACCTGGCAGCGG
631  ...........................................................................................C
631  ............................................................................................
631  ...................C........................................................................

GAGGGCCAGGACCAGAGCCAGGACATGGAGCTGGTGGAGACCAGGCCCTCAGGGGATGGGACCTTCCAGAAGTGGGCGGCCCTGGTGGTG
721  ............................................................................................
721  .....G......................................................................................
721  ............................................................................................

CCTCCTGGAGAGGAGCAGAGCTACACCTGCCATGTGCAGCACGAGGGCCTGCAGGAGCCCCTCACCCTGAGATGGGACCCTGCTCAGCCC
811  ............................................................................................
811  ................................................................................C...........
811  ............................................................................................

CCCGTCCCCATCGTGGGCATCATTGTTGGCCTGGTTCTXGTCCTGGTCGCTGGAGCCATGGTGGCTGGAGTTGTGATCTGGAGGAAGACG
901  ...........G........C................T......................................................
901  ................................C........A.......G........................................A.
901  ....................................G.......................................................

CGCTCAGGTGAAAAAGGAGGGAGCTACACTCAGGCTGCAGGCAGTGACAGTGCCCAGGGCTCCGATGTGTCCCTTACCAAGGATCCTAGA
991  ............................................................................................
991  .................................................................T..........................
991  ..................................................A.........................................

GTGTGA Majority
1081 ...... PA1
1081 ...... PC1
1081 ...... PD1
```

FIG. 1A

```
        ATGCGGGTCAGAGGCCCTCAAGCCATCCTCATTCTGCTGTCGGGGGCCCTGGCCCTGACCGGGACCCGGGCGGGTCCCCACTCCCTGAGG Majority
   1    ......................................................................................... PA14
   1    ........................................................................................C PC1
   1    ...................................................................A..................... PD1

TATTTCGACACCGCCGTGTCCCGGCCCGACCGCGGGGACTCCCGCTTCATCGCCGTCGGCTACGTGGACGACACGCAGTTCGTGCCGGTTC
  91    .....................................................C..A...............................A.....
  91    ......T..................................T...............................................
  91    ..............................GC....T.......AA...........................................

GACAGCGACGCCCCGAATCCGCGGATGGAGCCGCGGGCGCCCGTGGATACAGCAGGAGGGGCAGGAGTATTGGGATCGGGAGACACAGATC
 181    ....................A..GA..............................C.................................
 181    .................................G..A.................................................A
 181    ..................T...........................................A..A.C..G.G..A.

XXCAXGGACACCGCACAGACTTACCGAGTGGACCTGAACACCCTGCGCGGCTACTACAACCAGAGCGAGGCCGGGTCTCACACCCTCCAG
 271    AG..A...A.........................................A......................................
 271    CAA.G.......T...............G.............................................................
 271    GC..T..G..A........T........G.A.....CG...AGCT.T....................................A.....

AGCATGTACGGCTGCGACGTGGGACCAGACGGGCTCCTCCTCCGCGGGTACAGTCAGTTCGCCTACGACGGCGCCGATTACCTCGCCCTG
 361    ...................G............T....................T.G.................................
 361    .........T..T....................................A.......................................
 361    .T.................................................GA.........................A.........

AACGAGGACCTGCGCTCCTGGACCGCGGCGGACACGGCGGCTCAGATCTCCAAGCGCAAGTGGGAGGCGGCCAATGXGGCGGAGCAGGAG
 451    ..............................................................TT..T..A.......T...........
 451    ....................T.................................................C..................
 451    ..........................A.......................................G...A.........GTAG.

AGGAGCTACCTGCAGGGCCXGTGTGTGGAGTGGCTCCGCAGATACCTGGAGATGGGGAAGGACACGCTGCAGCGCGCAGAGCCTCCAAAG
 541    ......T........G..........................................................................
 541    ......G...................................................................................
 541    ......AC..............AG.A.......C........................................................

ACACATGTGACCCGCCACCCCAGCTCTGACCTGGGGGTCACCTTGAGGTGCTGGGCCCTGGGCTTCTACCCTAAGGAGATCTCCCTGACC
 631    ..........................................................................................
 631    ..........................................................................................
 631    .................C........................................................................

TGGCAGCGGGAGGGCCAGGACCAGAGCCAGGACATGGAGCTGGTGGAGACCAGGCCCTCAGGGGATGGGACCTTCCAGAAGTGGGCCGCC
 721    ..........................................................................................
 721    .......C..................................................................................
 721    ...................................C...............................................A.....

CTGGTGGTGCCTCCTGGAGAGGAGCAGAGCTACACCTGCCATGTGCAGCACGAGGGCCTGCAGGAGCCCCTCACCCTGAGATGGGACCCT
 811    .....................................................................................A...
 811    ..........................................................................................
 811    .........A..........................T...............A....................................

CCTCAGCCCCCCGTCCCCATCGTGGGCATCATTGTTGGCCTGGTTCTCGTCCTGGTCGCTGGAGCCATGGTGGCTGGAGTTGTGATCTGG
 901    ..A...................T..............................A......A............................
 901    ..........................................................................................
 901    .........T...........................G...............G...................................

AGGAAGAAGCGCTCAGGTGAAAAAGGAGGGAGCTACACTCAGGCTGCAGGCAGTGACAGTGCCCAGGGCTCCGATGTGTCCCTTACCAAG
 991    ....................................G.....................................................
 991    ..........................................................................................
 991    ..........................................................................................

GATCCTAGAGTGTGA Majority
1081    ............... PA14
1081    ............... PC14
1081    ............... PD14
```

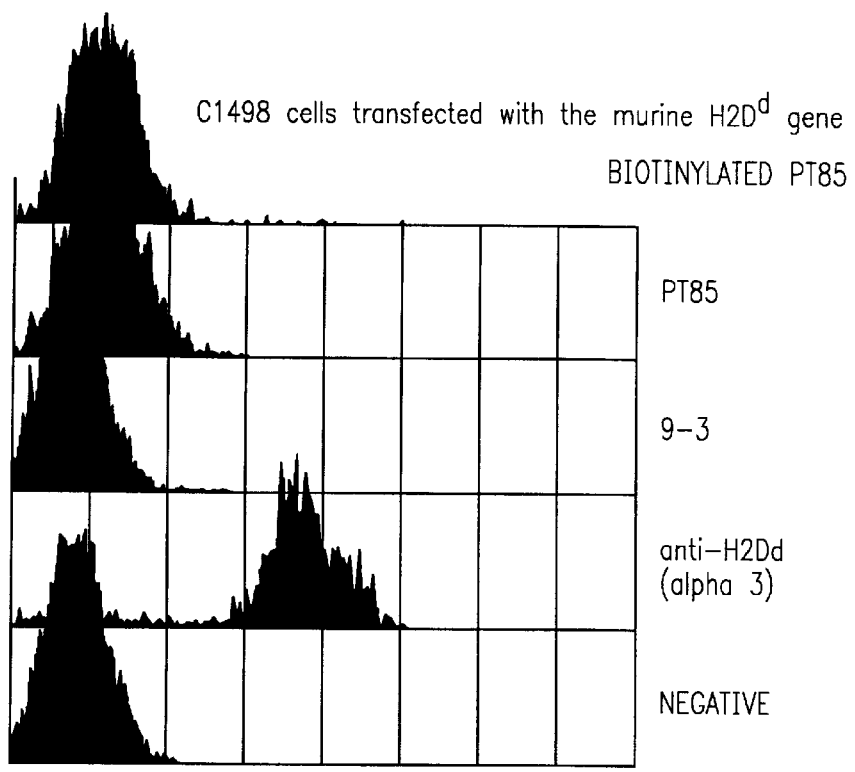
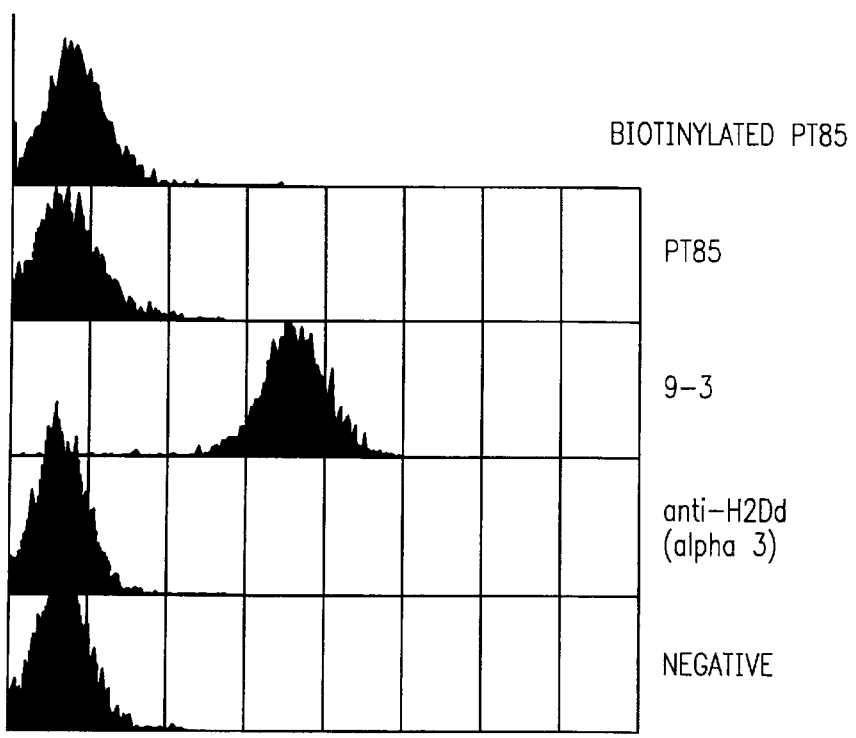

|  | 115 | 116 | 117 | 118 | 119 | 120 | 121 | 122 | 123 | 124 | 125 | 126 | 127 | 128 |
|---|---|---|---|---|---|---|---|---|---|---|---|---|---|---|
| HLA-A2.1 | Gln | Tyr | Ala | Tyr | Asp | Gly | Lys | Asp | Tyr | Ile | Ala | Leu | Asn | Glu |
| PD1 | Gln | Asp | Ala | Tyr | Asp | Gly | Ala | Asp | Tyr | Ile | Ala | Leu | Asn | Glu |
| PA1 | Gln | Asp | Ala | Tyr | Asp | Gly | Ala | Asp | Tyr | Ile | Ala | Leu | Asn | Glu |
| PC1 | Gln | Asp | Ala | Tyr | Asp | Gly | Ala | Asp | Tyr | Ile | Ala | Leu | Asn | Glu |
| PD14 | Gln | Asp | Ala | Tyr | Asp | Gly | Ala | Asp | Tyr | Ile | Ala | Leu | Asn | Glu |
| PA14 | Gln | Phe | Gly | Tyr | Asp | Gly | Ala | Asp | Tyr | Leu | Ala | Leu | Asn | Glu |
| PC14 | Gln | Phe | Ala | Tyr | Asp | Gly | Ala | Asp | Tyr | Leu | Ala | Leu | Asn | Glu |

FIG. 7A

|  | 223 | 224 | 225 | 226 | 227 | 228 | 229 | 230 | 231 | 232 | 233 | 234 | 235 |
|---|---|---|---|---|---|---|---|---|---|---|---|---|---|
| HLA-A2.1 | Asp | Gln | Thr | Gln | Asp | Thr | Glu | Leu | Val | Glu | Thr | Arg | Pro |
| PD1 | Asp | Gln | Ser | Gln | Asp | Met | Glu | Leu | Val | Glu | Thr | Arg | Pro |
| PA1 | Asp | Gln | Ser | Gln | Asp | Met | Glu | Leu | Val | Glu | Thr | Arg | Pro |
| PC1 | Asp | Gln | Ser | Gln | Asp | Met | Glu | Leu | Val | Glu | Thr | Arg | Pro |
| PD14 | Asp | Gln | Ser | Gln | Asp | Met | Glu | Leu | Val | Glu | Thr | Arg | Pro |
| PA14 | Asp | Gln | Ser | Gln | Asp | Met | Glu | Leu | Val | Glu | Thr | Arg | Pro |
| PC14 | Asp | Gln | Ser | Gln | Asp | Met | Glu | Leu | Val | Glu | Thr | Arg | Pro |

|  | 236 | 237 | 238 | 239 | 240 | 241 | 242 | 243 | 244 | 245 | 246 | 247 |
|---|---|---|---|---|---|---|---|---|---|---|---|---|
| HLA-A2.1 | Ala | Gly | Asp | Arg | Thr | Phe | Gln | Lys | Trp | Ala | Ala | Val |
| PD1 | Ser | Gly | Asp | Gly | Thr | Phe | Gln | Lys | Trp | Ala | Ala | Leu |
| PA1 | Ser | Gly | Asp | Gly | Thr | Phe | Gln | Lys | Trp | Ala | Ala | Leu |
| PC1 | Ser | Gly | Asp | Gly | Thr | Phe | Gln | Lys | Trp | Ala | Ala | Leu |
| PD14 | Ser | Gly | Asp | Gly | Thr | Phe | Gln | Lys | Trp | Ala | Ala | Leu |
| PA14 | Ser | Gly | Asp | Gly | Thr | Phe | Gln | Lys | Trp | Ala | Ala | Leu |
| PC14 | Ser | Gly | Asp | Gly | Thr | Phe | Gln | Lys | Trp | Ala | Ala | Leu |

FIG. 7B

|  |  | 77 | 78 | 79 | 80 |
|---|---|---|---|---|---|
| NK Clone 1 | HLA-Cw4 | Asn | Leu | Arg | Lys |
|  | PD1 | Gly | Leu | Asn | Thr |
|  | PA1 | Gly | Leu | Asn | Thr |
|  | PC1 | Asn | Leu | Lys | Asn |
|  | PD14 | Asn | Leu | Arg | Thr |
|  | PA14 | Asp | Leu | Asn | Thr |
|  | PC14 | Asp | Leu | Lys | Thr |

FIG. 8A

|  |  | 77 | 78 | 79 | 80 |
|---|---|---|---|---|---|
| NK Clone 2 | HLA-Cw3 | Ser | Leu | Arg | Asn |
|  | PD1 | Gly | Leu | Asn | Thr |
|  | PA1 | Gly | Leu | Asn | Thr |
|  | PC1 | Asn | Leu | Lys | Asn |
|  | PD14 | Asn | Leu | Arg | Thr |
|  | PA14 | Asp | Leu | Asn | Thr |
|  | PC14 | Asp | Leu | Lys | Thr |

FIG. 8B

|  |  | 77 | 78 | 79 | 80 | 81 | 82 | 83 |
|---|---|---|---|---|---|---|---|---|
| NK Clone 3 | HLA-B5801 | Asn | Leu | Arg | Ile | Ala | Leu | Arg |
|  | PD1 | Gly | Leu | Asn | Thr | Leu | Arg | Gly |
|  | PA1 | Gly | Leu | Asn | Thr | Leu | Arg | Gly |
|  | PC1 | Asn | Leu | Lys | Asn | Leu | Arg | Gly |
|  | PD14 | Asn | Leu | Arg | Thr | Ala | Leu | Gly |
|  | PA14 | Asp | Leu | Asn | Thr | Leu | Arg | Ser |
|  | PC14 | Asp | Leu | Lys | Thr | Leu | Arg | Gly |

FIG. 8C

PORCINE MHC CLASS I GENES AND USES THEREOF

BACKGROUND OF THE INVENTION

This invention is in the field of tissue and organ transplantation and immunological tolerance.

The induction of graft specific immunological tolerance is a much sought after goal as it would allow the transplantation of cells or organs without generalized immunosuppression. While a variety of procedures to induce graft specific tolerance have been proposed, non-specific immunosuppressive agents such as cyclosporin A and FK506 remain the agents of choice for treatment of patients undergoing transplantation. These agents allow the transplantation of "foreign" organs, but their immunosuppressive effect is accompanied by numerous side effects.including opportunistic infection, increased rate of neoplasm, and liver and kidney toxicity. Moreover, cyclosporin rarely allows long term graft function; the 10 year survival rate for allogeneic heart and kidney transplants has stabilized at about 50% [Kaufman and Ildstad (1994) Therapeutic Immunol. 1:101].

SUMMARY OF THE INVENTION

The invention is based on the discovery of six novel porcine MHC class I genes, the elucidation of their nucleotide sequences (SEQ ID NOS:1–6), and the deduction of the amino acid sequences (SEQ ID NOS:7–12) that they encode. These genes demonstrate a high degree of homology between each other and to MHC class I genes of other mammalian species. In addition, they are efficiently expressed when transferred to xenogeneic cells. These properties provide the basis for their use in establishing immunological tolerance in prospective transplant recipients prior to grafting with porcine cells, tissues or organs. Furthermore the genes and their products provide the components necessary for a variety of in vitro assays for screening transplant recipients and donors. Moreover, the polypeptides produced by the MHC class I genes of the invention can be used to prepare and screen a variety of useful antibodies.

Specifically, the invention features nucleic acid molecules that encode porcine MHC class I polypeptides which are at least 95% identical to the polypeptides PA1 (SEQ ID NO:7), PC1 (SEQ ID NO:8), PA14 (SEQ ID NO:10), or PC14 (SEQ ID NO:11). Also included in the invention are nucleic acid molecules that encode the porcine MHC class I polypeptides PA1 (SEQ ID NO:7), PC1 (SEQ ID NO:8), PD1 (SEQ ID NO:9), PA14 (SEQ ID NO:10), PC14 (SEQ ID NO:11), or PD14 (SEQ ID NO:12). The latter nucleic acid molecules can be pa1 (SEQ ID NO:1), pc1 (SEQ ID NO:2), pd1 (SEQ ID NO:3), pa14 (SEQ ID NO:4), pc14 (SEQ ID NO:5) or pd14 (SEQ ID NO:6).

The invention encompasses expression vectors containing these nucleic acid molecules, cell lines transfected with the expression vectors, the polypeptides encoded by the above nucleic acid molecules and antibodies specific for the polypeptides.

The invention features variant porcine MHC class I polypeptides in which one ore more of α1, α2, or α3 is deleted or replaced by the corresponding domain of a human or murine MHC class I polypeptide and variant porcine MHC class I polypeptides in which one or more amino acid residues has been replaced by the corresponding amino acid residue of a human MHC class I polypeptide. The invention also features the nucleic acid molecules encoding these variant MHC class I polypeptides.

Also provided is a method of preventing porcine graft rejection in a patient in which antibodies directed against a porcine MHC class I polypeptide are administered to a transplant recipient prior to or in conjunction with transplantation of porcine tissue or cells. This treatment may be given with or without immunosuppression. In addition, a method for inducing specific immunological tolerance in prospective transplant recipients is included in the invention. This method involves administering to the patient autologous cells transfected with and expressing the porcine MHC class I genes of the invention. These autologous cells are those expressing neither MHC class II polypeptides nor costimulatory molecules such as B7, e.g., fibroblasts, myoblasts, or keratinocytes. This prophylactic treatment may also be given with and without immunosuppression and may be used in prospective recipients of porcine cells, for example, pancreatic islets, hepatocytes, cardiac cells, corneal cells, neural cells, retinal cells, or myoblasts or porcine organs.

Also featured in the invention are assays to monitor tolerance in transplant recipients and for selecting an appropriate pig as a tissue donor. In one aspect, these assays involve testing patients for antibodies to porcine MHC class I polypeptides, including those of the invention. In a second aspect, lymphoid cells from the patient are tested for the presence of cytotoxic T lymphocytes by culturing the lymphoid cells with cells expressing the porcine MHC class I polypeptides or with purified porcine MHC class I polypeptides. The cultured cells are then tested for specific cytolytic activity against target cells expressing the porcine MHC class I polypeptide of interest. Also with the invention are methods for identifying, in a patient after tolerization, T cells (e.g., CD4+ cells) which react with porcine MHC class I. These methods entail contacting the T cells with a porcine MHC class I polypeptide and determining whether the T cells proliferate.

As used herein, "pa1, pc1, and pd1" are nucleic acid molecules corresponding to the aa, cc and dd alleles, respectively, of a porcine MHC class I gene referred to herein as p1.

As used herein, "pa14, pc14, and pd14" are nucleic acid molecules corresponding to the aa, cc and dd alleles, respectively, of a porcine MHC class I gene referred to herein as p14.

As used herein, "PA1, PC1, $PD_1$, PA14, PC14, and PD14" are porcine MHC class I polypeptides encoded by pa1, pc1, pd1, pa14, pc14, and pd14, respectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present application, including definitions, will control. In addition, the materials, methods, and examples described herein are illustrative only and not intended to be limiting.

Other features and advantages of the invention, e.g., prevention of graft rejection, will be apparent from the following detailed description, from the drawings and from the claims.

BRIEF DESCRIPTION OF THE DRAWINGS

FIG. 1A is a diagram showing the nucleotide sequences of the pa1 (SEQ ID NO:1), pc1 (SEQ ID NO:2) and pd1 (SEQ ID NO:3) porcine MHC class I cDNA genes. The sequences of the p1 clones are compared to a consensus (Majority) sequence (SEQ ID NO:35) derived from all three p1 sequences.

FIG. 1B is a diagram showing the nucleotide sequences of the pa14 (SEQ ID NO:4), pc14 (SEQ ID NO:5) and pd14 (SEQ ID NO:6) porcine MHC class I cDNA genes. The sequences of the p14 clones are compared to a consensus (Majority) sequence (SEQ ID NO:36) derived from all three p14 sequences. The p14 genes contain 3 codons in the signal peptide sequence that are not found in the p1 genes.

FIG. 2 is a diagram showing the deduced amino acid sequences of PA1 (SEQ ID NO:7), PC1 (SEQ ID NO:8), PD1 (SEQ ID NO:9), PA14 (SEQ ID NO:10), PC14 (SEQ ID NO:11) and PD14 (SEQ ID NO:12) aligned at the N-terminus of the α1 domain. A consensus (Majority) sequence (SEQ ID NO:37) is shown for comparison.

FIGS. 5A, 5B, 5C, 5D and 5E are flow cytometry histograms of murine lymphoma cells, (a) untransfected (FIG. 5A) and transfected with an expression vector containing cDNA encoding: (b) the porcine PD1 polypeptide (FIG. 5B); (c) the murine H2D$^d$ polypeptide (FIG. 5C); (d) the polypeptide illustrated in FIG. 4A (FIG. 5D); and (e) the polypeptide illustrated in FIG. 4B (FIG. 5E). The cells were stained with either G-3, PT-85, biotinylated PT-85, anti-H2D$^d$ (α3 domain) or M1/42 anti-mouse MHC class I primary antibodies.

FIGS. 7A and 7B are amino acid sequences (SEQ ID NOS:16–21) depicting critical residues for binding of human CD8 to MHC class I. The residues identified as binding sites for human CD8 are in the α2 (FIG. 7A) and α3 (FIG. 7B) domains. Residues shown to be required for binding are underlined. The residues found in the porcine class MHC class I genes are shown for comparison.

FIGS. 8A, 8B and 8C are amino acid sequences (SEQ ID NOS:22–34) depicting amino acids recognized by human NK cell receptors. The NK cell receptors responsible for the binding specificities shown have been designated p58 for NK clone 1 and NK clone 2 (FIGS. 8A and 8B) and NKB1 for NK clone 3 (FIG. 8C). Residues identified as critical for binding of the inhibitory receptors are underlined. The porcine sequences present at these sites are shown below the human sequence.

DETAILED DESCRIPTION

A. Overview

Figure 3A:
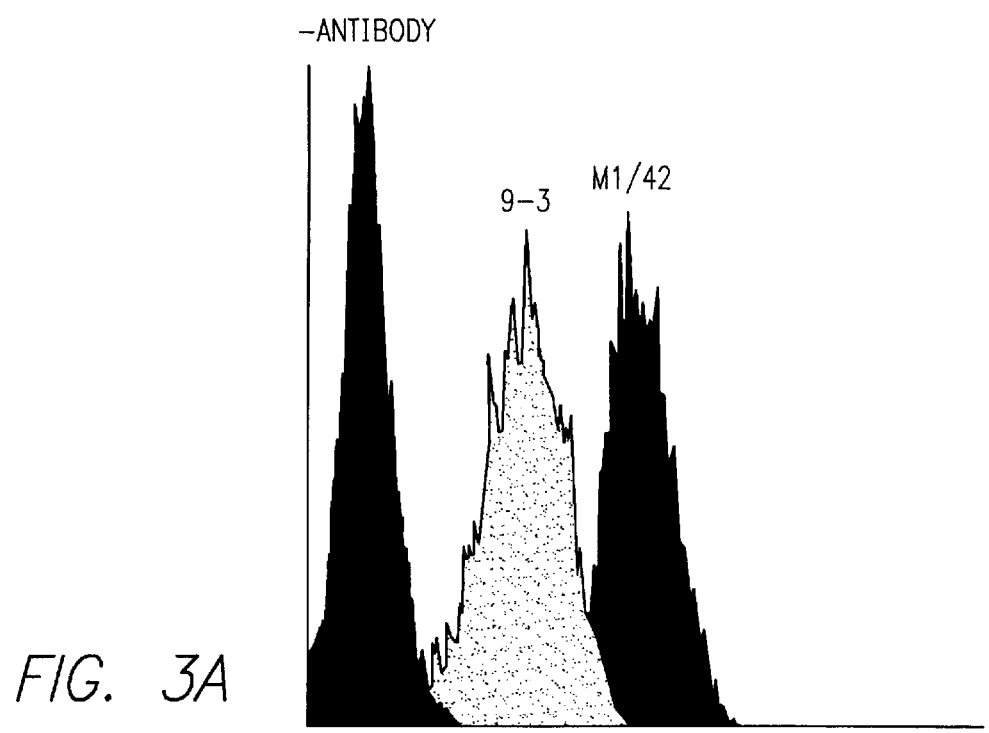
FIG. 3A is a flow cytometry histogram depicting expression of PD1 on mouse lymphoma cells transfected with an expression vector containing pd1. The cells were stained with anti-porcine MHC class I primary antibody, 9-3, and anti-mouse MHC class I primary antibody, M1/42. Controls without primary antibody are shown.

When tissues from another member of the same species (allogeneic tissue) or from different species (xenogeneic tissue) are transplanted into a mammal, a vigorous multifactorial immune response ensues that, in the absence of intervention, culminates in immunological rejection of the tissue. The antigens of the graft that are primarily involved in eliciting this response are the polypeptides encoded by the MHC. Furthermore, the MHC class I molecules are the principal "targets" of the effector arm of this extremely potent, tissue-destructive immune response. However, exposure, in an appropriate manner, of the recipient mammal to MHC class I molecules expressed by the graft prior to transplantation, can result in specific immunological tolerance to those MHC class I molecules and consequent enhanced survival of the graft.

Described below is the cloning and molecular characterization of three haplotypes (aa, cc, and dd) of two porcine MHC class I genes (p1 and p14) (SEQ ID NOS:1–6). The genes of the invention can be used to create human cells expressing porcine MHC class I genes. These cells can be used to induce specific tolerance to porcine grafts and to screen transplant recipients. The proteins encoded by the genes of the invention can be utilized in assays to screen recipients subsequent tolerization and/or transplantation for the presence of graft-specific antibodies and cytotoxic T lymphocytes. The polypeptides of the invention (and variants thereof) can be used to generate a variety of useful antibodies.

The method of the invention entails administering human cells expressing porcine MHC class I to a human recipient of a porcine cell or tissue transplant prior to transplantation. Without being bound by any particular theory, it appears that the administration of human cells expressing porcine MHC class I induces tolerance to porcine tissue or cells as follows. Cytotoxic T cells or the precursors cells that are destined to develop into cytotoxic cells encounter the xenogeneic MHC or a chimeric MHC on a cell that is otherwise identical to self. Help is not available from T cells that would normally recognize an array of other antigens presented by professional antigen presenting cells at the site of inflammation. The interaction of xenoreactive T cells and transfected porcine MHC in the absence of help tolerizes the T cells so that subsequent transplantation of pig cells does not lead to rejection.

In the tolerization method of the invention, the availability of foreign antigens to be processed and presented by recipient antigen presenting cells are restricted and are thereby prevented from recruiting helper T cells that would be needed to provide the stimulus for proliferation of the cytotoxic cells. The cells that express mutated or chimeric MHC molecules are recognized by the xenoreactive T cells, but, due to low affinity binding, prevent activation of T cell precursors and amplification of the response. This is in contrast to the case of a fully xenogeneic graft which, in addition to endogenous MHC class I polypeptides, contains an array of foreign antigens that are processed and presented by MHC class II polypeptides on recipient antigen presenting cells, resulting in the activation of CD4+ cells that produce cytokines and support the proliferation of CD8+ cells. In the absence of this help, it is proposed that the subset of T cells that would otherwise react with the graft is inactivated. These cells do not proliferate upon subsequent exposure to pig MHC class I polypeptides on the surface of porcine cells in the graft. Furthermore, it is proposed that the occurrence of self peptides on the foreign MHC class I provides a unique signal to the recipient immune system that results in tolerance. Thus, in contrast to the situation in an infection or a transplant in which foreign peptides are presented on self MHC class I, or a graft in which foreign peptides are presented on foreign and self MHC, the transfected target cells contain self peptides on the foreign MHC class I. T cells that are tolerant to these self peptides in the context of self MHC class I may maintain that tolerance in the context of the foreign MHC class I and transfer tolerance to other T cells.

The above described mechanisms of action are merely exemplary and it is emphasized that the present invention is not limited by a particular mechanism of action.

Figure 2:
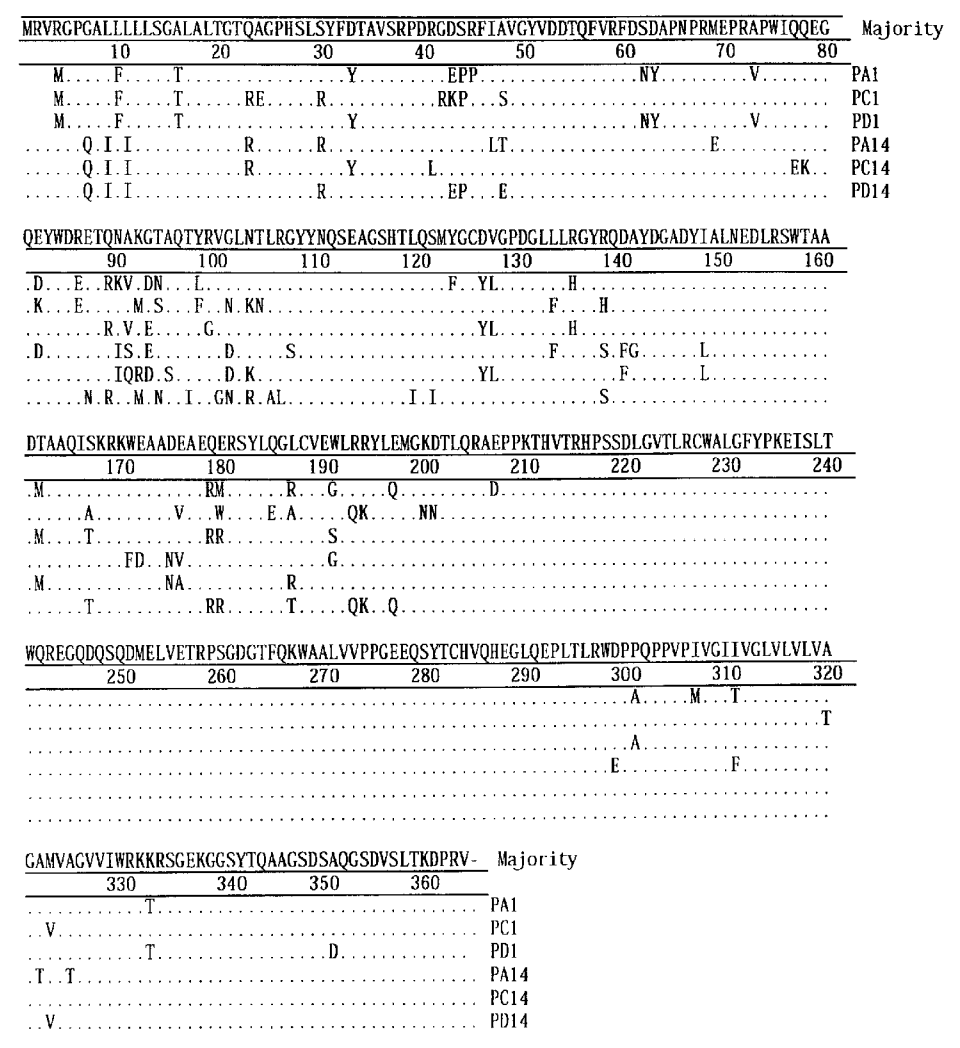

B. Nucleic Acid Molecules, Vectors, Expression Vectors and Transfected Cell Lines B.1: Nucleic Acid Molecules One aspect of the invention features nucleic acid molecules that encode proteins which are at least 95% identical to the polypeptides selected from the group consisting of PA1 (SEQ ID NO:7), PC1 (SEQ ID NO:8), PA14 (SEQ ID NO:10), or PC14 (SEQ ID NO:11) (FIG. 2). Another embodiment of the invention includes nucleic acid molecules that encode PA1 (SEQ ID NO:7), PC1 (SEQ ID NO:8), PD1 (SEQ ID NO:9), PA14 (SEQ ID NO:10), PC14 (SEQ ID NO:11) or PD14 (SEQ ID NO:12). These nucleic acids can be pa1 (SEQ ID NO:1), pd1 (SEQ ID NO:2), pd1 (SEQ ID NO:3) (FIG. 1A) and pa14 (SEQ ID NO:4), pc14 (SEQ ID NO:5) and pd14 (SEQ ID NO:6) (FIG. 1B) or degenerate variants thereof.

Another embodiment of the invention includes variants of all of the above nucleic acid molecules which lack the region encoding the α3 domain of the porcine MHC class I polypeptides and variants in which the sequence encoding one or more of domains α1, α2, and α3 is replaced with a sequence encoding the corresponding domain of a murine or human MHC class I polypeptide. Such variant MHC class I polypeptides are also referred to as chimeric MHC class I polypeptides.

The invention also encompasses nucleic acids encoding variant porcine MHC class I protein in which one or more amino acid residues have been replaced by the corresponding residue of human MHC class I.

The signal sequences of 24 amino acids for the p14 genes and 21 amino acids for the p1 genes precedes the α1 domain (start at position 25 for alignment of the p1 and p14 genes). The α1 domain consists of residues 25–114, the α2 domain of residues 115–206, the α3 domain of residues 207–298, and the transmembrane and cytoplasmic domains of residues 299–364.

The porcine MHC class I nucleic acid molecules of the invention thus include: (a) nucleic acid molecules having the sequence of SEQ ID NOS: 1, 2, 3, 4, 5 or 6; (b) nucleic acid molecules that encode a polypeptide with the amino acid sequences with SEQ ID NOS: 7, 8, 9, 10, 11 or 12; (c) any nucleotide sequences that hybridize to the complement of the DNA sequences with SEQ ID NOS:1, 2, 3, 4, 5 or 6 under highly stringent conditions, for example, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. [Ausubel F. M. et al., eds., (1989) Current Protocols in Molecular Biology, Vol. I, Green Publishing Associates, Inc., and John Wiley & sons, Inc., New York] and encodes functionally equivalent gene products; and (d) any nucleotide sequence that hybridizes to the complement of the DNA sequences that encode polypeptide with the amino acid sequences with SEQ ID NOS:7, 8, 9, 10, 11 or 12 under stringent conditions. The invention also includes degenerate variants of sequences (a) through (d).

The invention also includes nucleic acid molecules, preferably DNA molecules, that hybridize to, and are therefore the complements of, the nucleotide sequences (a) through (d), in the preceding paragraph. Such hybridization conditions may be highly stringent, as described, above or less highly stringent, such as moderately stringent conditions for example washing in 0.2×SSC/0.1% SDS at 42° C. [Ausubel et al., supra]. In instances wherein the nucleic acid molecules are deoxyoligonucleotides ("oligos"), highly stringent conditions may refer, for example, to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as porcine MHC class I porcine MHC class I antisense molecules, useful, for example, in porcine MHC class I gene regulation (for and/or as antisense primers in amplification reactions of porcine MHC class I gene nucleic acid sequences). Still further, such molecules may be used as components of screening methods whereby, for example, the presence of a particular porcine MHC class I allele, may be detected.

In addition to the nucleotide sequences described above, full length genomic sequences can be identified and readily isolated, without undue experimentation, by molecular biological techniques well known in the art. The invention encompass these nucleic acid molecules.

B.2: Vectors and Expression Vectors

The invention also encompasses: (a) DNA vectors that contain any of the foregoing porcine MHC class I (or variant porcine MHC class I) coding sequences and/or their complements (i.e., antisense); and (b) DNA expression vectors that contain any of the foregoing porcine MHC class I (or variant MHC class I) coding sequences. An expression vector is composed of or contains a nucleic acid in which a polynucleotide sequence encoding a peptide or polypeptide of the invention is operatively linked to a promoter or enhancer-promoter combination. A promoter is a transcriptional regulatory element composed of a region of a DNA molecule typically within 100 nucleotide pairs in front (upstream of) of the point at which transcription starts. Another transcriptional regulatory element is an enhancer. An enhancer provides specificity in terms of time, location and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region. To bring a coding sequence under control of a promoter, it is necessary to position the translation initiation site of the translational reading frame of the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trD system, the TAC system, the TRC system, the major operator and promoter regions of phage A, the control regions of fd coat protein, the promoter for 3-phosphoglycerate kinase, the promoters of acid phosphatase, and the promoters of the yeast a-mating factors.

Expression vectors and methods for their construction are known to those familiar with the art (Ausubel et al., supra). Suitable vectors include plasmids, and viral vectors such as herpes viruses, retroviruses, canary pox viruses, adenoviruses and adeno-associated viruses, among others.

B.3: Transfected Cell Lines

The invention includes cell lines transfected with expression vectors containing the porcine MHC class I encoding sequences described in Section B.1, supra. Cells to be used for transfection include, but are not restricted to, murine lymphoma cell lines, murine fibroblasts, murine L cells, murine muscle lines and primary human fibroblasts, human keratinocytes, and human myoblasts. Cells are transfected by a variety of methods commonly used in the art, for example, electroporation or calcium phosphate precipitation. Genes can also be introduced into the cells by transduction with viral vectors, e.g., retroviruses. Successfully transfected cell lines are selected by appropriate means familiar to those of average skill in the art, e.g., using tissue culture medium supplemented with a drug such as Geneticin™ (G418) for which the relevant expression vector contains a resistance gene. Successfully transfected cell lines are screened for cell-surface expression of the porcine MHC class I molecules by a variety of possible methods, e.g., flow cytometry analysis (FCA).

C. Antibodies to Episodes Within the Amino Acid Sequences of SEQ ID NOS: 7, 8, 9, 10, 11 OR 12

Antibodies that specifically recognize epitopes within the amino acid sequence of SEQ ID NOS:7, 8, 9, 10, 11 or 12 are also encompassed by the invention. Such antibodies include but are not limited to polyclonal antibodies, monoclonal antibodies, humanized or chimeric antibodies, single chain antibodies, Fab fragments, F(ab')$_2$ fragments, and epitope-binding fragments of any of the above.

The antibodies of the invention can be used, for example, in the prevention of rejection in a recipient of a graft expressing relevant porcine MHC class I polypeptides. They can also be used to define the MHC class I polypeptides expressed by outbred pigs, and may therefore be utilized as part of a screening technique to select an appropriate pig as a donor for a given prospective porcine graft recipient. Such antibodies may also be utilized in the screening assays of the invention.

C.1: Production and Screening of Antibodies

For the production of antibodies of the invention, a host animal is immunized by injection with either a polypeptide containing the amino acid sequence of SEQ ID NOS:7, 8,.9, 10, 11 or 12 or a portion thereof (e.g., an $\alpha 1$, $\alpha 2$, or $\alpha 3$ domain alone or as part of a chimeric porcine MHC class I polypeptide) or with cells expressing such a polypeptide on their surface. Such host animals may include but are not limited to rabbits, mice, and rats, to name but a few. Various adjuvants may be used to increase the immunological response, depending on the host species, including but not restricted to Freund's (complete and incomplete) adjuvant, mineral gels such as aluminum hydroxide, lysolecithin, pluronic polyols, polyanions, peptides, oil emulsions, BCG (bacille Calmette-Guerin) and *Corynebacterium parvum*. Polyclonal antibodies are heterogeneous populations of antibody molecules derived from the sera of the immunized animals.

In order to further enhance immunogenicity, the immunogen may be coupled to a carrier. Examples of such carriers are keyhole limpet hemocyanin (KLH) and bovine serum albumin (BSA). Other albumins such as ovalbumin, mouse serum albumin or rabbit serum albumin can also be used as carriers. Methods of coupling a peptide to a carrier are well known in the art and include the use of glutaraldehyde, carbodiimide and m-maleimidobenzoyl-N-hydroxysuccinimide ester.

The amount of antigen to be used can be determined readily by those with average skill in the art without undue experimentation. The antigen can be administered by a number of routes (subcutaneous, intramuscular, intradermal, intravenous and intraperitoneal). The production of polyclonal antibodies is monitored by sampling blood of the immunized animal at various time points after administration. When the desired level of antibody is obtained, the animal is bled and the serum is stored.

Monoclonal antibodies, which are homogeneous populations of antibodies to a particular antigen, may be obtained by any technique which provides for the production of antibody molecules by continuous cell lines in culture. These include, but are not limited to, the hybridoma technique [Kohler and Milstein (1975) Nature 256:495–497; U.S. Pat. No. 4,376,110; Howell and Lane (1988) Antibodies, A Laboratory Manual, Cold Spring Harbor Press, N.Y.], the human B-cell hybridoma technique [Kosbor et al. (1983) Immunology Today 4:72; Cole et al. (1983) Proc. Natl. Acad. Sci. USA 80:2026], and the EBV-hybridoma technique [Cole et al. (1985), Monoclonal Antibodies And Cancer Therapy, Alan R. Liss, Inc.]. Such antibodies may be of any immunoglobulin class including IgG, IgM, IgE, IgA, IgD and any subclass thereof.

In addition, techniques developed for the production of "chimeric antibodies" can be used [Morrison et al. (1984) Proc. Natl. Acad. Sci. USA 81:6851; Neuberger et al. (1984) Nature 312:604; Takeda et al. (1985) Nature 314:452]. These involve splicing a portion of a gene encoding a mouse antibody of appropriate antigen specificity to a portion of a gene encoding a human antibody of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies [U.S. Pat. No. 4,946,778; Bird (1988) Science 242:423; Huston et al. (1988) Proc. Natl. Acad. Sci. USA 85:5879; and Ward et al. (1989) Nature 334:544] can be adapted to produce single chain antibodies against the epitopes of SEQ ID NOS:7, 8, 9, 10, 11 or 12. Single chain antibodies are formed by linking the heavy and light chain fragments of the Fv region via an amino acid bridge, resulting in a single chain polypeptide. They are conveniently produced by recombinant DNA techniques.

Antibody fragments which recognize specific epitopes may be generated by known techniques. For example, such fragments include but are not limited to the F(ab')$_2$ fragments which can be produced by pepsin digestion of the antibody molecule, and the Fab fragments which can be generated by reducing the disulfide bridges of the F(ab')$_2$ fragments. Alternatively, Pab expression libraries may be constructed [Huse et al. (1989) Science 246:1275] to allow rapid and easy identification of monoclonal Fab fragments with the desired specificity.

Under some circumstances it may be useful to generate antibodies against a specific domain(s) of porcine MHC class I, e.g., the $\alpha 1$ and $\alpha 2$ domains. Accordingly, a polypeptide having only the porcine $\alpha 1$ and $\alpha 2$ domains may be injected into a host animal for the purpose of antibody production. Alternatively, one might inject a chimeric porcine MHC class I in which one or more porcine MHC class I domains is replaced by the corresponding domain from host MHC class I.

Methods for screening antibodies for binding specificity are well known in the art. These include, but are not restricted to, testing for: (a) binding to cells expressing a polypeptide of SEQ ID NOS:7, 8, 9, 10, 11 or 12; (b) lack of binding to cells expressing a polypeptide of SEQ ID NOS:7, 8, 9, 10, 11 or 12 except the polypeptide of interest; (c) binding to a polypeptide of SEQ ID NOS:7, 8, 9, 10, 11 or 12; (d) lack of binding to all the polypeptides of SEQ ID NOS:7, 8, 9, 10, 11 or 12 except the polypeptide of interest; and (e) specific inhibition of binding to polypeptides of SEQ ID NOS:7, 8, 9, 10, 11 or 12 by peptides corresponding to the polymorphic region of the polypeptide of interest.

C.2: Prevention of Graft Rejection by Antibodies to Polypeptides with SEO ID NOS:7, 8, 9, 10, 11 or 12

Antibodies of the invention can be used to mask porcine MHC class I present on the surface of transplanted porcine tissue or cells in order to reduce transplant rejection. For example, the method described in Faustman U.S. Pat. No. 5,283,058 (and U.S. Ser. No. 08/112,709) may be used in conjunction with these antibodies. The antibodies may be used in conjunction with porcine grafts expressing MHC class I polypeptides of SEQ ID NOS:7, 8, 9, 10, 11 or 12 or other porcine MHC class I. Moreover, several different antibodies may be combined for use in this method. Antibodies are administered in a purified form. Methods for purifying antibodies are well-known in the art [Howell and Lane, cited supra], e.g., immunoaffinity purification using staphylococcal protein A immobilized on a solid support. Special care is taken to remove toxic and inflammatory substances such as bacterial endotoxin. Traditional immunosuppressive therapy such as cyclosporin, FK506, or anti-lymphocyte serum treatment The masking antibodies can also be administered directly to the patient along with the graft tissue or cells. It is well known in the medical arts that dosages for any one patient depend on many factors, as well as the particular compound to be administered, the time and route of administration and other drugs being administered concurrently. Dosages for the antibodies of the invention will vary, but can be, when administered intravenously, approximately 0.04 mg to 10 mg/ml blood volume. Routes and doses of administration are well known to skilled pharmacologists and physicians. Routes include, but are not restricted to: intraperitoneal, intramuscular, intrapulmonary, transmucosal, subcutaneous intradermal and intravenous. Methods of assessing the efficacy of the treatment will be the same as those described in Section E infra.

D. In Vitro Screening Assays for Antibodies and Cytotoxic T Lymphocytes Specific for Porcine MHC Class I Polypeptides The invention encompasses in vitro systems to test for the presence of antibodies and cytotoxic T lymphocytes (CTL) specific for porcine MHC class I polypeptides. Such assays would serve to monitor the effectiveness of the specific immunotolerization protocols of the invention both before and after transplantation by testing for the presence of (a) antibodies to porcine MHC class I molecules, and/or (b) CTL specific for porcine MHC class I molecules. For example, one might attempt to induce specific immunotolerance by administering cells expressing one or more of the MHC class I polypeptides of the invention. Prior to transplantation or subsequent to transplantation, the methods described below could be used to determine to what extent, if any, the potential transplant recipient or transplant recipient has produced antibodies or CTL directed against the porcine MHC class I used for immunotolerization or other porcine MHC class I.

D.1: Screening Assay Using Porcine MHC Class I Polypeptide Expressing Cells

Cells expressing one or more defined endogenous porcine MHC class I polypeptides, e.g., inbred pig peripheral blood mononuclear cells (PBMC) or cells expressing one or more exogenous porcine MHC class I molecules encoded by transfected or transduced expression vectors can be used to screen for antibodies to porcine MHC class I molecules in a biological fluid, for example, of a porcine graft recipient. The cells can be cell lines transfected or transduced with expression vectors containing nucleic acids encoding porcine MHC class I polypeptides that are at least 95% identical to polypeptides with SEQ ID NOS:7, 8, 10 or 11, cell lines transfected or transduced with expression vectors containing nucleic acids with SEQ ID NOS:1, 2, 3, 4, 5 or 6 and expressing cell-surface polypeptides with SEQ ID NOS:7, 8, 9, 10, 11 or 12, or transfected cell lines expressing a variant (e.g., chimeric) MHC class I polypeptide.

The cells are contacted with a potential source of antibody ("primary antibody"). After co-incubation, unbound material is removed. Bound antibody can then be detected by addition of a detectably labeled "secondary" antibody that specifically recognizes the primary test antibody. Methods for detectably labeling polypeptides are described infra. After co-incubation, unbound substances are removed and any secondary antibody that remains bound is detected by any number of techniques well-known in the art. In a preferred embodiment, the secondary antibody is detectably labeled with a fluorochome, e.g., fluorescein, and bound secondary antibody is detected by FCA or by fluorescence microscopy. Other techniques for detecting bound secondary antibodies are described infra.

Instead of using a detectably labeled secondary antibody, an unlabeled secondary antibody can be used. After incubation, unbound antibody is removed and a detectably labeled "tertiary" antibody that specifically recognizes the secondary antibody is added. After incubation and removal of unbound detectably labeled tertiary antibody, the presence of the bound detectably labeled tertiary antibody is detected by FCA, fluorescence microscopy or one of the methods described infra.

Alternatively, the secondary antibody may be conjugated to biotin by methods known to those of average skill in the art. In this case, bound biotinylated secondary antibody is contacted with detectably labeled avidin and avidin which remains bound to the biotin and thus to the cells after washing is detected by FCA, fluorescence microscopy or one of the methods described infra.

Instead of using biotinylated secondary antibody, the tertiary antibody may be conjugated to biotin. In this case, bound biotinylated tertiary antibody is contacted with detectably labeled avidin and avidin which remains bound to the biotin and thus to the cells is detected by FCA, fluorescence microscopy or one of the methods described infra.

In these assays binding of primary test antibody to the cells expressing the porcine MHC class I polypeptide and not to control cells that do not express the MHC class I polypeptide is an indication of the presence of at least one antibody specific for the porcine MHC class I polypeptide in the test source.

One of the ways in which a protein (e.g., an antibody or some other secondary reagent such as avidin) can be detectably labeled is by linking it to an enzyme for use in an enzyme immunoassay (EIA) [Voller (1978), The Enzyme Linked Immunosorbent Assay (ELISA), Diagnostic Horizons 2:1 (Microbiological Associates Quarterly Publication, Walkersville, Md.); Voller, et al. (1978) J. Clin. Pathol. 31:507; Butler (1981) Meth. Enzymol. 73:482; Maggio (ed.) (1980) Enzyme Immunoassay, CRC Press, Boca Raton, Fla.; Ishikawa, et al. (eds.) (1981) Enzyme Immunoassay, Kgaku Shoin, Tokyo]. The enzyme which is bound to the antibody will react with an appropriate substrate, preferably a chromogenic substrate, in such a manner as to produce a chemical moiety that can be detected, for example, by spectrophotometric, fluorimetric or visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, betagalactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling appropriate polypeptides, it is possible to detect bound material through the use of a radioimmunoassay (RIA) [see, for example, Weintraub (1986), Principles of Radioimmunoassay, Seventh Training Course on Radiolig and Assay Techniques, The Endocrine Society]. The radioactive isotope can be detected by such means as the use of a gamma counter or a scintillation counter, or by autoradiography.

It is also possible to label with a fluorescent compound. When the fluorescently labeled material is exposed to light of the proper wave length, its presence can be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

Proteins can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The polypeptides also can be detectably labeled by coupling to a chemiluminescent compound. The presence of the chemiluminescent-tagged antibody is then determined by detecting the presence of luminescence that arises during the course of a chemical reaction. Examples of particularly useful chemiluminescent labeling compounds are luminal, isoluminol, theromatic acridinium ester, imidazole, acridinium salt and oxalate ester.

Likewise, a bioluminescent compound may be used to label the relevant proteins. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase, and aequorin.

D.2: Screening Assay Using Porcine MHC Class I Polypeptides

Isolated porcine MHC class I polypeptides or portions or variants thereof can also be used to screen for antibodies to porcine MHC class I polypeptides.

These porcine MHC class I polypeptides can be those with at least 95% identity to those with SEQ ID NOS:7, 8, 10 or 11, or those having the sequence of SEQ ID NOS:7, 8, 9, 10, 11 or 12. Also included in the invention are variants of all the above polypeptides (e.g., chimeric porcine MHC class I).

The polypeptides can also be (i) naturally occurring porcine MHC class I polypeptides, (ii) truncated forms of such polypeptides lacking transmembrane domains or (iii) fusion proteins containing (i) or (ii).

In one aspect of the invention, porcine MHC class I polypeptide is provided bound to a solid support. Examples of solid supports are given infra. Unbound porcine MHC class I polypeptide is removed from the solid support (e.g., by washing) and the bound porcine MHC class I polypeptide is contacted with a source of porcine MHC class I polypeptide-specific antibody (primary test antibody). After co-incubation, unbound substances are removed and bound antibody is detected by addition of a detectably labeled secondary antibody that specifically recognizes the primary test antibody. Methods for detectably labeling polypeptides are described supra. After co-incubation, unbound secondary antibody is removed and in any secondary antibody that remains is detected by one of the methods described supra.

Instead of using a detectably labeled secondary antibody, an unlabeled secondary antibody can be used. After incubation, unbound antibody is removed and a detectably labeled tertiary antibody that specifically recognizes the secondary antibody is added. After incubation and removal of unbound detectably labeled tertiary antibody, the presence of the bound detectably labeled tertiary antibody is detected by one of the methods described supra.

Alternatively, the secondary antibody may be conjugated to biotin by methods known to those of average skill in the art. In this case, bound biotinylated secondary antibody is contacted with detectably labeled avidin and avidin which remains bound to the biotin and thus to the solid support after washing is detected by one of the methods described supra.

Instead of using biotinylated secondary antibody, the tertiary antibody may be conjugated to biotin. In this case, bound biotinylated tertiary antibody is contacted with detectably labeled avidin and avidin which remains bound to the biotin and thus to the solid support is detected by one of the methods described supra.

In this assay, binding of primary test antibody to a porcine MHC class I polypeptide and not to control polypeptides, e.g., other porcine MHC class I polypeptides or albumin, is an indication of the presence of at least one antibody specific for the porcine MHC class I polypeptide in the test source.

Well known solid supports that may be used for screening assays of the invention include, but are not restricted to, glass, polystyrene, polypropylene, polyethylene, dextran, nylon, natural and modified celluloses, and polyacrylamides. In practice, microtiter plates may conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In the assays described, the presence of certain antibodies specific for a particular porcine MHC class I polypeptide, would indicate that the induced specific immunotolerance is not complete.

D.3: Polypeptides

The invention features substantially pure polypeptides which are at least 95%, 98%, or 99% identical to the porcine MHC class I polypeptides PA1 (SEQ ID NO:7), PC1 (SEQ ID NO:8), PA14 (SEQ ID NO:10), or PC14 (SEQ ID NO:11). The invention also encompasses the porcine MHC class I polypeptides PA1 (SEQ ID NO:7), PC1 (SEQ ID NO:8), PD1 (SEQ ID NO:9), PA14 (SEQ ID NO:10), PC14

(SEQ ID NO:11), or PD14 (SEQ ID NO:12) as well as variants thereof (e.g., chimeric porcine MHC class I). Thus, the polypeptides of the invention include porcine MHC class I polypeptides in which one or more domains (α1, α2, or α3) have been replaced by the corresponding human or murine MHC class I domain. Human MHC class I sequences are described by Parham et al. (Proc. Natl. Acad. Sci., USA 85:4005).

The term "substantially pure", as used herein, refers to porcine MHC class I polypeptide which is substantially free of other proteins, lipids, carbohydrates or other materials with which it is naturally associated. One skilled in the art can purify porcine MHC class I polypeptide using standard techniques for protein purification. [Protein Purification, Principles and Practice, second edition (1987) Scopes, Springer Verlag, N.Y.]

Where a particular polypeptide is said to have a specific percent identity to a reference polypeptide of a defined length, the percent identity is relative to the reference polypeptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. For the porcine MHC class I polypeptides, the length of the reference polypeptide sequence will generally be at least 50 amino acids, preferably 100 amino acids and more preferably full length. Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

The invention includes a functional polypeptide, porcine MHC class I, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. "Functional fragments" of the porcine MHC class I polypeptide, includes fragments of porcine MHC class I polypeptide as long as the activity of porcine MHC class I polypeptide remains, e.g., binding of porcine MHC class I polypeptide specific antibody. Smaller peptides containing the biological activity of porcine MHC class I are included in the invention. One of skill in the art can assay for functional activity of porcine MHC class I by standard methods, e.g., ELISA or Western blot assay.

Minor modifications of the porcine MHC class I polypeptide primary amino acid sequence may result in proteins which have substantially equivalent activity as compared to the naturally occurring porcine MHC class I polypeptide described herein. Such modifications may be deliberate, as by site-directed mutagenesis, or may be spontaneous. All of the polypeptides produced by these modifications are included herein as long as the biological activity of porcine MHC class I polypeptide is present, e.g., binding of porcine MHC class I polypeptide specific antibody. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for porcine MHC class I polypeptide activity.

In the case of porcine MHC class I polypeptides of the invention which are less than 100% identical to a reference sequence, the non-identical positions are preferably, but not necessarily, conservative substitutions for the reference sequence. The term "conservative substitution" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative substitution" also includes the use of a substituted amino acid in place of an unsubstituted parent amino acid provided that antibodies raised to the substituted polypeptide also immunoreact with the unsubstituted polypeptide.

Peptides and polypeptides used in the screening assays of the invention may be obtained by a variety of means. Smaller peptides (less than 50 amino acids long) may be conveniently synthesized by standard chemical methods. Some polypeptides (e.g. "secondary" or "tertiary" antibodies) may be purchased from commercial sources. Where otherwise unavailable, antibodies can be generated as described in Section C supra. Detectably labeled antibodies either can be purchased from commercial sources or are readily prepared by those of ordinary skill in the art.

The porcine MHC class I polypeptides may also be produced in their naturally occurring, truncated, or fusion protein forms by recombinant DNA technology using techniques well known in the art. In order to facilitate secretion from host cells, the invention features expression systems in which the nucleic acid sequence encoding the transmembrane domain of porcine MHC class I polypeptides has been deleted.

Methods include, for example, in vitro recombinant DNA techniques, synthetic techniques, and in vivo genetic recombination. See, for example, the techniques described in Sambrook et al. (1989) Molecular Cloning, A Laboratory Manual, Cold Spring Harbor Press, N.Y.; and Ausubel et al., eds. (1989), Current Protocols in Molecular Biology, Green Publishing Associates, Inc., and John Wiley & Sons, Inc., N.Y. Alternatively, RNA encoding the proteins may be chemically synthesized. See, for example, the techniques described in Oligonucleotide Synthesis, (1984) Gait, M. J. ed., IRL Press, Oxford, which is incorporated by reference herein in its entirety.

A variety of host-expression vector systems may be utilized to express the nucleotide sequences. Where the peptide or polypeptide is soluble, it can be recovered from: (a) the culture, i.e., from the host cell in cases where the peptide or polypeptide is not secreted; or (b) from the culture medium in cases where the peptide or polypeptide is secreted by the cells. The expression systems also encompass engineered host cells that express the polypeptide in situ, i.e., anchored in the cell membrane. Purification or enrichment of the polypeptide from such an expression system can be accomplished using appropriate detergents and lipid micelles and methods well known to those skilled in the art. Alternatively, such engineered host cells themselves may be used in situations where it is important not only to retain the structural and functional characteristics of the protein, but also to assess biological activity.

The expression systems that may be used for purposes of the invention include but are not limited to microorganisms such as bacteria (for example, *E. coli* and *B. subtilis*) transformed with recombinant bacteriophage DNA, plasmid DNA or cosmid DNA expression vectors containing the nucleotide sequences; yeast transformed with recombinant yeast expression vectors; insect cells infected with recombinant viral expression vectors (baculovirus); plant cell systems infected with recombinant viral expression vectors (e.g., cauliflower mosaic virus, CaMV; tobacco mosaic virus, TMV) or transformed with recombinant plasmid expression vectors; or mammalian cells (e.g., COS, CHO, BHK, 293, 3T3) harboring recombinant expression constructs containing promoters derived from the genome of mammalian cells (e.g. metallothionein promoter) or from mammalian viruses.

In bacterial systems, a number of expression vectors may be advantageously selected depending upon the use intended for the gene product being expressed. For example, when a large quantity of such a protein is to be produced, e.g. for raising antibodies to the protein, vectors which direct the expression of high levels of fusion protein products that are readily purified may be desirable. Such vectors include, but are not limited to, the *E. coli* expression vector pUR278 [Ruther et al. (1983) EMBO J. 2:1791], in which the coding sequence may be ligated individually into the vector in frame with the lacZ coding region so that a fusion protein is produced; pIN vectors [Inouye & Inouye (1985) Nucleic Acids Res. 13:3101; Van Heeke & Schuster (1989) J. Biol. Chem. 264:5503]; and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts [e.g., See Logan & Shenk (1984) Proc. Natl. Acad. Sci. USA 81:3655]. Specific initiation signals may also be required for efficient translation of inserted nucleotide sequences. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. [Bittner et al. (1987) Methods in Enzymol. 153:516].

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Appropriate cell lines or host systems can be chosen to ensure the correct modification and processing of the foreign protein expressed. Mammalian host cells include but are not limited to CHO, VERO, BHK, HeLa, cos, MDCK, 293, 3T3, and WI38.

For long-term, high-yield production of recombinant proteins, stable expression is preferred. For example, cell lines which stably express the sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the gene product. Such engineered cell lines may be particularly useful in screening and evaluation of compounds that affect the endogenous activity of the gene product.

A fusion protein may be readily purified by utilizing an antibody or a ligand that specifically binds to the fusion protein being expressed. For example, a system described by Janknecht et al. [(1991) Proc. Natl. Acad. Sci. USA 88:8972] allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. If desired, the histidine tag can be selectively cleaved with an appropriate enzyme.

D.4: In Vitro Screening Assay for Cytotoxic T Lymphocytes (CTL) Specific for Porcine MHC Class I Polypeptide Expressing Cells Lymphoid cells, e.g., from peripheral blood, spleen, lymph nodes, Peyer's patches, or peritoneum can be screened for the presence of CTL specific for porcine MHC class I polypeptides. In a preferred embodiment, these MHC class I polypeptides are those with at least 95% identity to those with SEQ ID NOS:7, 8, 10 or 11. In a more preferred embodiment these porcine MHC class I polypeptides are those with the amino acid sequences of SEQ ID NOS: 7, 8, 9, 10 11 or 12.

"Responder" lymphocytes obtained from a graft recipient or prospective graft recipient which has been subjected to specific immunotolerization are co-cultured with metabolically inhibited, e.g., exposed to x or γ irradiation or treated with mitomycin-C, "stimulator cells" expressing a test cell-surface porcine MHC class I polypeptide, e.g. porcine lymphoid cells porcine fibroblasts or fibroblasts of the recipient harboring an expression vector that encodes the test porcine MHC class I polypeptide. These "activation" cultures can be supplemented with "helper" factors, e.g. interleukin-2 (IL-2). After five to ten days of culture, the "activation mixture" is harvested and viable cells are counted by dye exclusion light microscopy using a dye that only stains non-viable cells, e.g., trypan blue. The activation mixture is then tested for the presence of CTL in a cell-mediated lympholysis (CML) assay familiar to those of ordinary skill in the art, e.g, the $^{51}$Cr-release CML assay. The cells from the activation mixture ("effectors") are cultured at various effector to target cell ratios, with $^1$Cr-labeled "target cells" expressing the same porcine MHC class I polypeptide as the stimulator cells used for the activation culture, e.g., porcine lymphoid cells, porcine fibroblasts or fibroblasts derived from the prospective recipient and harboring an expression vector encoding a porcine MHC class I polypeptide. After four to eights hours of culture, equal fractions of culture supernatant, e.g., 100 μl, are removed from each culture vessel, e.g., the wells of a 96-well microtiter culture plate. Percent specific lysis is calculated using the formula:

$$\% \text{ Specific Lysis} = \frac{\text{Experimental Release} - \text{Spontaneous release}}{\text{Maximum Release} - \text{Spontaneous release}} \times 100$$

where "Experimental Release" is the radioactivity released from target cells in the presence of effector cells, "Spontaneous release" is the radioactivity released from target cells in the presence of culture medium without effectors and "Maximum release" is the radioactivity released from target cells in the presence of 0.1N hydrochloric acid.

In this assay, specific lysis of target cells expressing the test porcine MHC class I polypeptide by effectors generated in activation cultures containing stimulator cells expressing the test porcine MHC class I polypeptide but not by effectors generated in activation cultures containing control stimulator cells not expressing the test porcine MHC class I polypeptide, e.g., stimulator cells expressing either no porcine MHC class I polypeptides or a porcine MHC class I polypeptide distinct from the test porcine MHC class I polypeptide, would be an indication of the presence of CTL specific for the test MHC class I polypeptide in the transplant recipient or prospective transplant recipient from which the responder lymphoid cells were derived. The specificity of the CTL activity can be further tested for by using control target cells not expressing the test porcine MHC class I polypeptide. Such target cells would not be lysed by CTL specific for the test polypeptide.

E. Induction of Immunological Tolerance to Porcine Grafts

Tolerance to transplanted tissues will be induced with cells that share a matching MHC class I haplotype with the recipient organism but have been transfected with the gene for normal or variant (e.g., chimeric) pig MHC class I polypeptides. Preferably, but not necessarily, the cells used to induce tolerance will express a MHC class I of the same haplotype as the porcine cells or organ to be transplanted. The cells that will be used to induce tolerance lack the characteristics of professional antigen presenting cells such as expression of MHC class II or costimulatory molecules such as B7. By using a cell of matching MHC haplotype to the recipient, the complication of allogeneic rejection of the injected cell is avoided. The introduction of the tolerizing cell line can be performed in conjunction with short term cyclosporin or FK506 therapy or treatment with anti-lymphocyte serum to prevent rejection; such therapies have been shown to be synergistic with DST and to aid in the induction of tolerance. A mouse cell line transfected with an expression vector encoding a porcine MHC class I polypeptide will be used to induce tolerance to porcine MHC-bearing cells in murine studies. In humans, cells from the recipient will be removed by biopsy and transfected with the constructs expressing one or more porcine MHC class I (e.g., PA1, PC1, PD1, PA14, PC14, PD14, or variants thereof, or other porcine MHC class I). These cells will be reintroduced into the recipient prior to transplantation of a porcine graft.

Porcine MHC class I polypeptides to be expressed in transfected cells are any of the polypeptides of the invention or variants thereof or other porcine MHC class I. Cells expressing mutated forms of these porcine MHC class I polypeptides will also be used to induce tolerance by promoting low affinity interactions with the xenoreactive T cells. These constructs will include MHC molecules that are missing the α3 domain to prevent interaction with recipient CD8 on the CTL and thereby prevent high affinity interactions, as well as chimeric MHC class I polypeptides produced by rearrangement of the exons that encode mouse or human α3 domains. These hybrid molecules will interact with host lymphocytes, but antigen will be presented in the peptide binding groove of pig α1 and α2 domains. The chimeric molecules will promote tolerance to porcine MHC by placing the foreign part of the molecule in the context of self MHC where it should come into contact with T cells that are tolerant to self. Also useful are chimeras in which a α1, α2, or α3 domain has been replaced by the corresponding human MHC class I domain.

The cell lines to be used for this new approach to the induction of immunological tolerance to porcine tissues would have the advantage that a single transfected cell line could potentially be effective in prolonging graft acceptance for a variety of therapeutic porcine cell types. The porcine donor cells or tissues to be transplanted after tolerization with donor MHC would need to have a limited expression of other histocompatibility antigens (e.g., MHC class II) and would therefore ideally be depleted of lymphocytes prior to transplantation. Among the cells which meet these criteria are hepatocytes, neural cells and islets. The method is also useful in conjunction with organ transplantation.

E.1: Animal Studies

Several cell lines have been generated that express cell surface porcine MHC class I polypeptides after transfection with expression vectors encoding nucleic acids of the invention. The transfected cell lines harbor three different cDNA molecules corresponding to porcine MHC class I genes: the first cDNA is prepared from RNA from outbred swine tissue by reverse transcriptase polymerase chain reaction (RTPCR) using primers corresponding to 5' and 3' sequences from the porcine MHC class I gene, pd1; the second cDNA (SEQ ID NO:3) is prepared from dd haplotype of inbred swine using primers derived from pd1; and the third (SEQ ID NO:6) is.made from inbred swine (dd) using primers derived from the swine class I gene pd14.

The porcine MHC class I genes are inserted into the expression vector pcDNA3 (Invitrogen) at HindIII/XbaI sites and expression of the message is driven by a TK promoter spliced into this vector. Cells are transfected with this construct by electroporation; control cells are transfected with vector alone. Stable cell lines are selected in G418 containing medium and cloned by limiting dilution after enrichment using magnetic beads with attached monoclonal porcine MHC class I specific antibody, 9-3.

For mouse experiments a number of cell lines have been transfected and shown to express porcine MHC class I genes at the cell surface by FCA with anti-porcine MHC class I polypeptide-specific antibodies, PT-85 and 9-3. These include a mouse lymphoma cell line, C1498, which is concordant with C57B1 mice (H2$^b$); fibroblasts derived from BALB/c mice (H2$^d$); and mouse L cells which are concordant at MHC with C3H mice (H2$^k$). In addition a number of other cell lines (fibroblast, lymphoma, muscle) of known H2 haplotype can be used with inbred recipients.

The animal is injected with the transfected cell line that differs from the recipient only in the expression of porcine MHC class I. One or two weeks after injection of various cell numbers the animal is transplanted with porcine cells (e.g., neural cells, cardiac cells, myoblasts, retinal cells, corneal cells, islets, or hepatocytes). In initial experiments intravenous injection is employed, but other sites may prove equally effective. Administration of cells to these sites can include, for example, injection into the subcapsular space of the kidney, intrathymic injection [Posselt et al. (1990) Science 249:1293; Sayegh et al. (1993) Transplantation 56:401], subcutaneous injection, intraportal injection [Goss et al. (1994) J. Clin. Invest. 93:1312; Nagano et al. (1993) Transplantation Proc. 25:352] or injection into the site of the intended transplant. The time interval between injection of the tolerogenic cell and the transplantation can also be varied. An interval of two weeks is used in the initial experiments. The survival of the porcine cells is assessed by methods used to assess graft function and survival, e.g., (RIA) for porcine insulin or C-peptide in the case of islets, ELISA or Western blots for porcine albumin for hepatocytes, histology, or in situ hybridization. Controls will include a) animals injected with the cell line without transfection; b) animals injected with the cell line transfected with an irrelevant gene; and c) untreated animals. The survival of the graft in immunosuppressed animals (cyclosporin) or nude mice will serve as a positive control for graft acceptance.

Cells for transplantation are preferably derived from inbred minipigs of matching haplotype to the porcine MHC class I expressed by the transfected cell used to induce tolerance. In initial experiments, the transplanted cells express the same MHC class I polypeptides as the tolerogenic cell line. If this approach prolongs survival of the graft, cells from different haplotypes or outbred pigs will be assessed for ability to survive in the treated host.

E.2: Induction of Tolerance to Porcine Cells in Humans

As MHC class I in humans (HLA) displays extensive polymorphism, HLA matched cell lines are not available for transfection with porcine MHC class I genes. For the application of porcine MHC class I-bearing cells as a method of inducing tolerance to pig tissues in humans, cells used for the induction of tolerance need to be harvested from the recipient (e.g. primary human fibroblasts, human keratinocytes, and human myoblasts). These cells are maintained in culture and the porcine MHC class I gene is introduced by transfection followed by expansion in culture. Expansion in culture can be carried out using methods related to those described by Grossman et al. [(1994) Nature Genetics, 6:335] and Raper et al. [(1996) Annals of Surg. 223:116].

It has been shown that human T cells are capable of directly recognizing porcine MHC class I polypeptides. These xenoreactive cells are tolerized by placing the porcine MHC class I polypeptides in the context of autologous cells that lack other foreign antigens. In the absence of antigens to be presented by professional antigen presenting cells, the T cell help needed for expansion of the T cells that lead to rejection is not available, leading to tolerance by the host for the transplanted porcine cells.

The transfected cells are used to induce tolerance to porcine grafts by similar methods as described for the animal experiments. The cells, after transfection and culture are injected intravenously into the recipient prior to transplantation of porcine cells. If necessary, short term cyclosporin, FK506 or anti-lymphocyte therapy is used to prevent rejection of the cells bearing the foreign porcine MHC class I antigen. The route of administration will be the same as for the animal experiments.

The cells used for transfection of porcine MHC class I are, for example, fibroblasts obtained by skin biopsy of the recipient. The human fibroblasts are expanded in culture and transfected with a vector containing a cDNA nucleic acid encoding porcine MHC class I polypeptides. A negative screen for expression of MHC class II and B7 molecules is performed to ensure that the transfection does not result in upregulation of undesired gene products. The expression of porcine MHC class I polypeptides on the cell surface is assessed by FCA with antibodies specific for porcine MHC class I molecules. Binding of iodinated antibodies with the same specificity determines the number of MHC class I molecules per cell. The cells are injected into the patient by the methods found most suitable in animal studies (see Section E.1 supra). Two weeks after the tolerizing injection, the patient receives a porcine cell transplant. These cells are haplotype-matched to the porcine MHC class I encoding nucleic acid employed for transfection of the tolerizing, or, if the animal studies indicate that tolerance can be induced to multiple haplotypes, the cells (e.g., islets, hepatocytes, myoblasts, neural cells, cardiac cells, retinal cells, or corneal cells) are obtained from outbred donors. It is understood that tolerance can also be induced with cells transfected with and expressing more than one porcine MHC class I gene (p1, p14, or p6, for example). Such genes can also be more than one allele (aa, cc, or dd, for example). The patients are tested for xenograft acceptance using the same protocols as for animals (see Section E.1 supra). This method is an alternative means of inducing porcine specific tolerance that should be applicable for the transplantation of various porcine cell types and organs.

EXAMPLES

The following procedures and their use in the exemplary studies described below are meant to illustrate the invention and not to limit it.

Isolation and Sequencing of Porcine MHC Class I cDNA

Total RNA was isolated from either porcine smooth muscle cells (aa and dd haplotype miniature swine) or from porcine peripheral blood lymphocytes (cc haplotype) using RNAzol B™ following the manufacturer's protocol (Tel-Test, Inc.). The first strand of cDNA was generated using 1 ug of total RNA primed with oligo dT by reverse transcription (Clontech 1st-Strand cDNA Synthesis Kit). PCR was carried out using 5' primers designed from the genomic sequence for pd1 and pd14 [Satz et al. (1985) J. Immunol. 135:2167] with restriction sites for Hind III and Xho I indicated: 5'-ATCGAAGCTTATGGGGCCTGGAGCCCTC TTCCTG-3' (SEQ ID NO:13) for the 5' primer of the p1 genes and 5'-ATCGAAGCTTATGCGGGTCAGAG GCCCTCAAG CCATCCTCATTC-3' (SEQ ID NO:14) for the 5' primer for the p14 genes. The 3' primer for both cDNAs was 5'-CGATCTCGAGTCACACTCTAGGAT CCTTGGGTA AGGGAC-3' (SEQ ID NO:15]. PCR was performed by a "touchdown" method [Don et al. (1991) Nucleic Acids Res. 19:4008; Roux (1994) Biotechniques 16:812] method in which denaturation was carried out at 94° C., and annealing was performed at temperatures ranging from 72° C. to 60° C. for 1 min with 2 cycles at each temperature followed by 10 cycles at 60° C. PCR products were cloned into pGem7Zf (+) (Promega) for sequencing using Sequenase Version 2.0 (USB). Both strands of DNA were sequenced. Multiple PCR reactions were performed to obtain independent clones for each gene, and at least two clones corresponding to each gene were sequenced for confirmation of the reported sequences.

Restriction Digest Analysis

The porcine MHC class I cDNA clones were analyzed by restriction mapping as follows: 1 ug of DNA (porcine MHC class I clone in pGem7Zf) was digested with Hind III and Xho I at 37° C. for 2 hours or with BsmB I at 55° C. for 2 hours. Products were separated on 1% agarose gels (Gibco) and stained with ethidium bromide.

Transfection

The porcine MHC class I genes were inserted at Hind III/XbaI I sites into pcDNA3 (Invitrogen) which was modified to contain a thymidine kinase promoter. The mouse lymphoma cell line C1498 ($H-2^b$) was utilized. Electroporation was carried out at 270 V, 960 uF using 50 ug DNA and $10^7$ cells in serum free RPMI medium. Cells were grown in DMEM containing 10% fetal calf serum and were selected beginning 48 h after transfection in 800 ug/ml G418. Media was changed every two days and after three weeks, pd1 and pd14 transfected cells were selected with anti-mouse IgG conjugated magnetic beads (Dynal) coated with anti-porcine MHC class I antibody 9-3. Two weeks later these cells underwent a second round of magnetic bead selection. This cell population was cloned by limiting dilution into 96 well plates. Control cells were transfected with vector alone. Positive PD1 and PD14 expressing clones were screened by FCA with a FACScan (Becton Dickinson) using anti-porcine MHC class I antibodies, PT-85 (VMRD) and 9-3 at a concentration of 1 ug/$2\times10^5$ cells. Fluorescein-conjugated donkey antimouse IgG (Jackson) was added for detection. Cells were incubated with antibody for 1 h at 4° C. in PBS containing 0.5% bovine serum albumin (BSA) and after addition of secondary antibody were further incubated for 30 min. at 4° C. As a control for $H2^b$ expression, the cells were tested with anti-H2 antibody, M1/42.

Example 1

Isolation and Sequencing of MHC Class I Genes from Homozygous aa, cc or dd Pigs

RNA isolated from inbred miniature swine of three haplotypes was reverse transcribed and amplified employing primers for p1 and p14 genes. Six cDNAs were obtained (a p1 and p14 product from each haplotype), and the cDNAs were compared by digestion with restriction enzymes. The distinct patterns obtained for the products derived from p1 and p14 specific primers indicated that clones corresponding to the p1 and p14 loci from each of the three haplotypes had been derived, and the genes were therefore designated by their locus and haplotype as pa1 (SEQ ID NO:1), pd1 (SEQ ID NO:2), pd1 (SEQ ID NO:3), and pa14 (SEQ ID NO:4), pc14 (SEQ ID NO:5) and pd14 (SEQ ID NO:6). The successful reverse transcription demonstrated that both genes were expressed in porcine cells.

Within each locus the cDNA sequences of the three haplotypes displayed a high degree of homology (FIG. 1A and 1B). Comparison of the pairs of haplotypes within p1 indicated an average of 55 nucleotide differences out of 1086 bases with a range of 31–67 differences. A similar comparison at the p14 locus yielded an average of 64 differences with a range of 43–80. Comparison of pairs of HLA alleles within a much larger sample of HLA-A, B and C loci gave an average value of 35 differences with a range of 1–85 [Parham et al. (1995) Immunol. Rev. 143:141].

Homology between the two loci was of a similar magnitude. Comparison of each pair of p1 and p14 genes yielded an average of 68 nucleotide differences between the loci with a range of 52–79. This compares with an average of 104 differences and a range of 55–141 found for HLA genes [Parham et al. (1995), cited supra].

The deduced amino acid sequence of the two loci (SEQ ID NOS:7–12) (FIG. 2) indicated that the extensive homology observed among the haplotypes of each locus was also evident between the two loci. All six genes shared considerable sequence, particularly in the α3 domain and transmembrane and cytoplasmic regions. P14 (SEQ ID NO:10–12) contained three additional amino acids at the N-terminus of the leader sequence that confirmed the identity of the three genes as p14 alleles [Satz et al., cited supra].

Example 2

Expression of Porcine MHC class I on the Cell Surface of Mouse Lymphoblasts

Figure 3B:
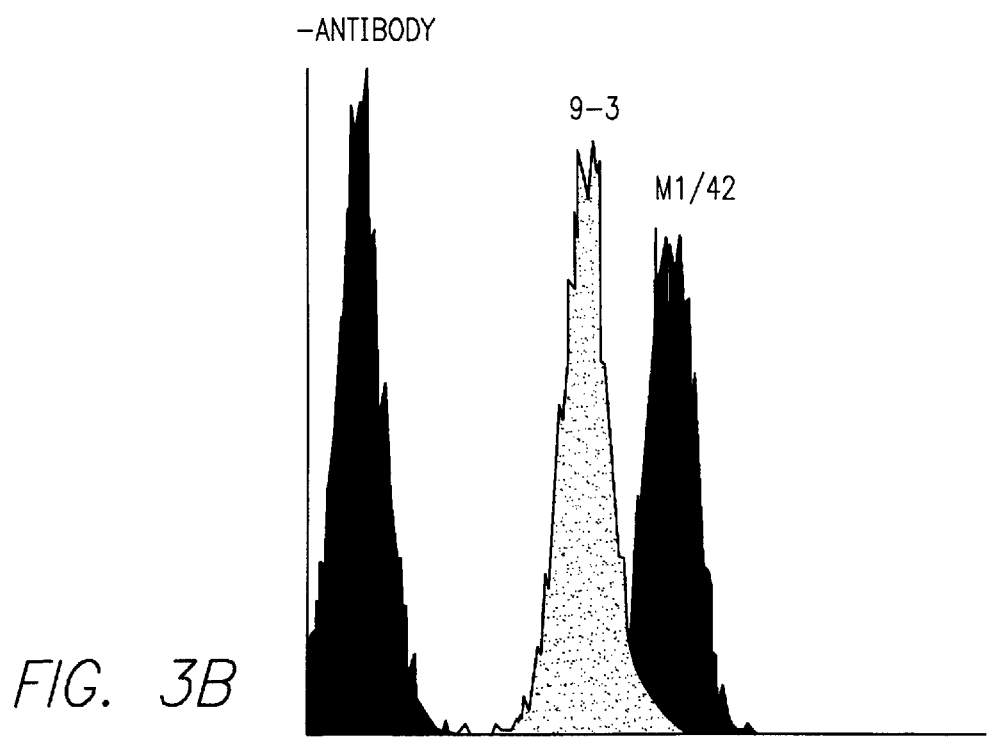
FIG. 3B is a flow cytometry histogram depicting expression of PD14 on mouse lymphoma cells transfected with an expression vector containing pd14. The cells were stained with anti-porcine MHC class I primary antibody, 9-3, and anti-mouse MHC class I primary antibody, M1/42. Controls without primary antibody are shown.

The cDNAs for two of the porcine MHC class I genes were transfected into mouse cell lines to determine whether the clones would be expressed. In each case expression could be seen as detected with an antibody, 9-3, against a monomorphic determinant in the α3 domain of porcine MHC class I polypeptides (FIG. 3). An antibody, PT-85, specific for a determinant on porcine MHC class I polypeptides that is dependent on the conformation of the molecule, reacted with the PD1 and PD14 expressed on the C1498 cells.

Figure 4A:
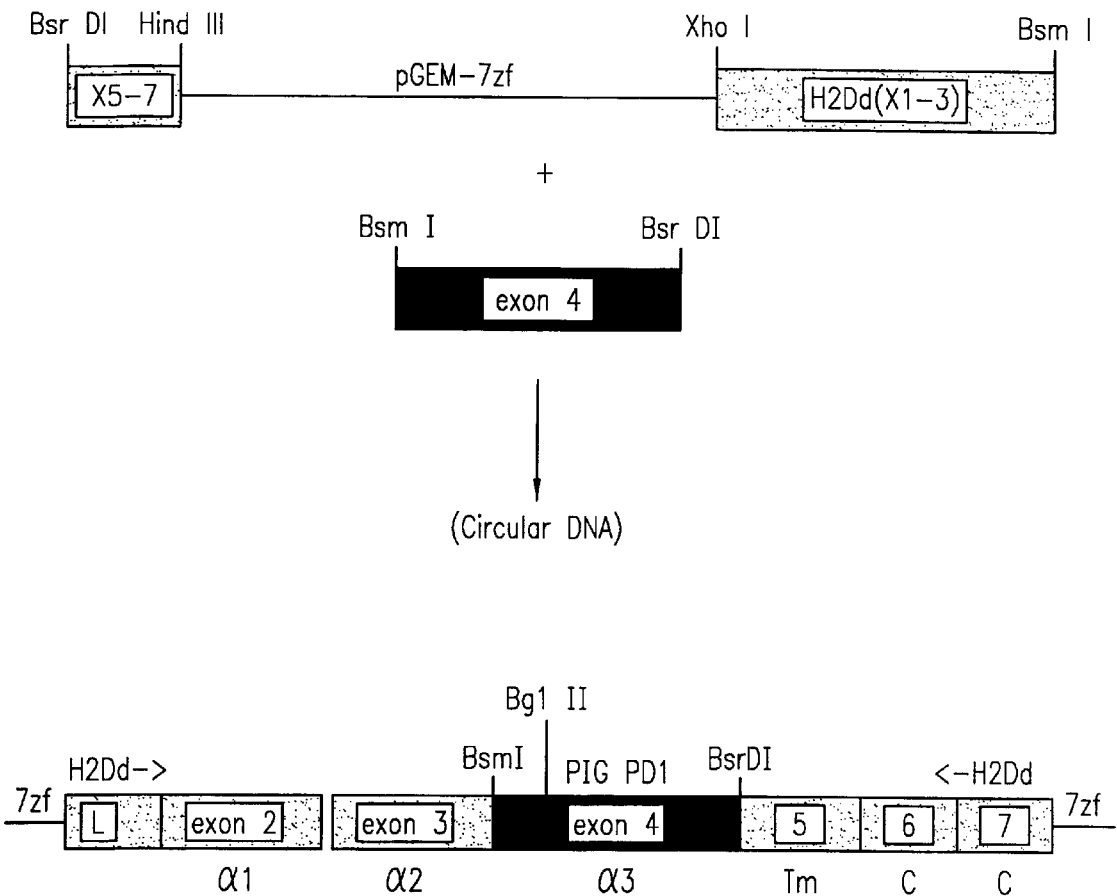
FIG. 4A and 4B are schematic diagrams of polypeptides encoded by chimeric cDNA constructs. The chimeric constructs encode polypeptides containing: (a) the leader, α1, α2, transmembrane and cytoplasmic domains of the murine MHC class I polypeptide H2D$^d$ and the α3 domain of the porcine MHC class I polypeptide PD1 (FIG. 4A); and (b) the leader, α3, transmembrane and cytoplasmic domains of H2D$^d$ and α1 and α2 domains of PD1 (FIG. 4B).
Figure 4B:
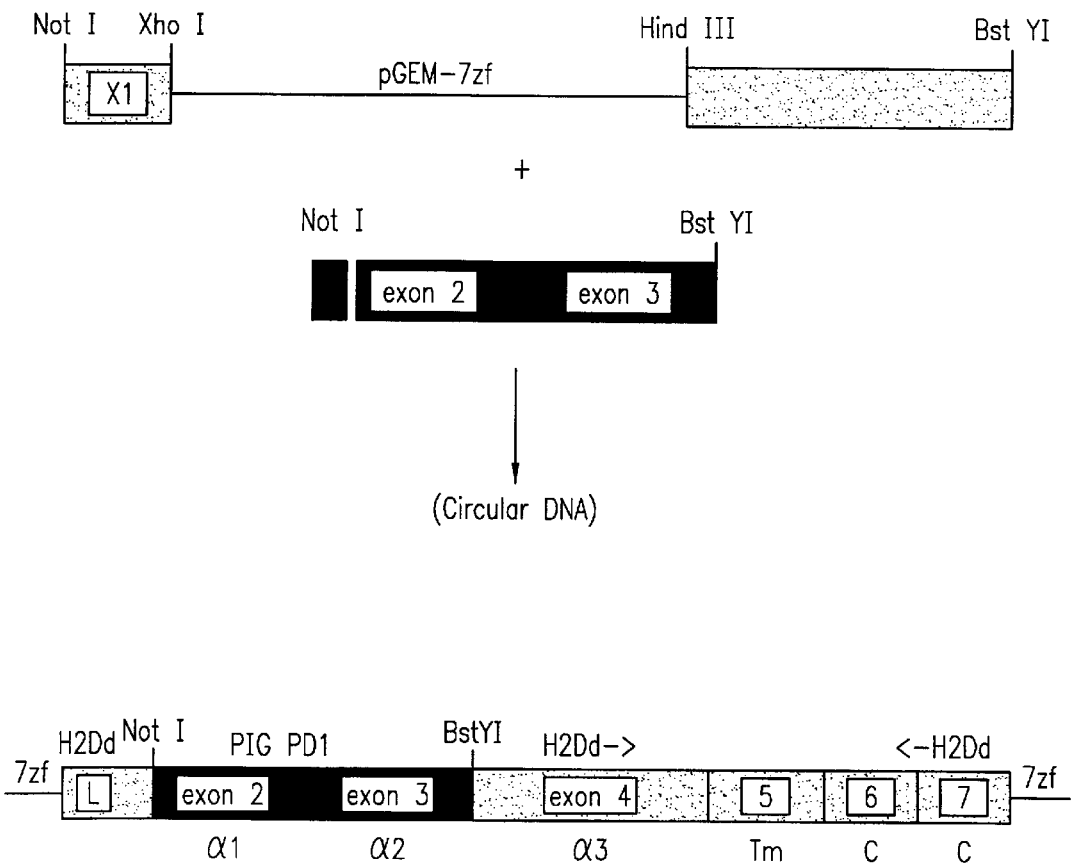
Figure 5A:
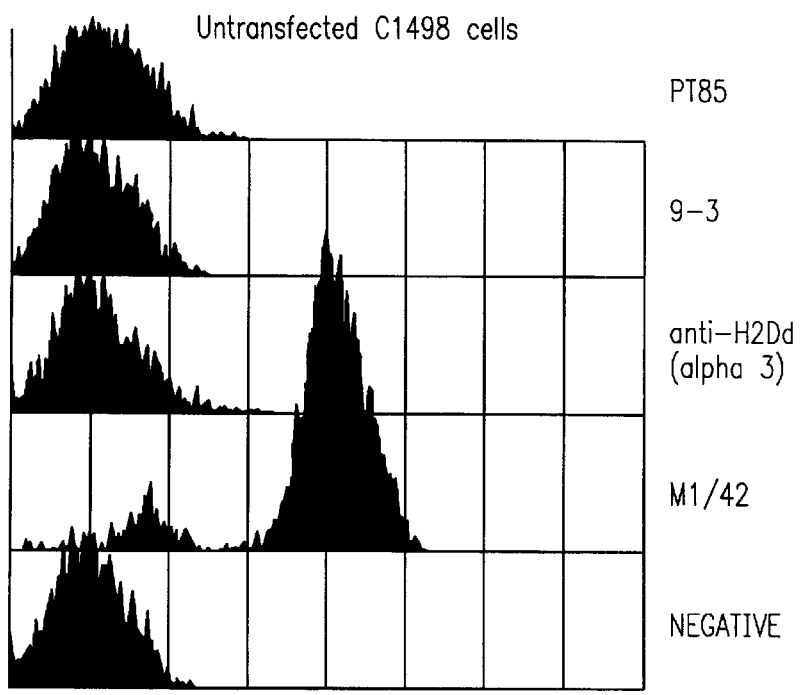
Figure 5B:
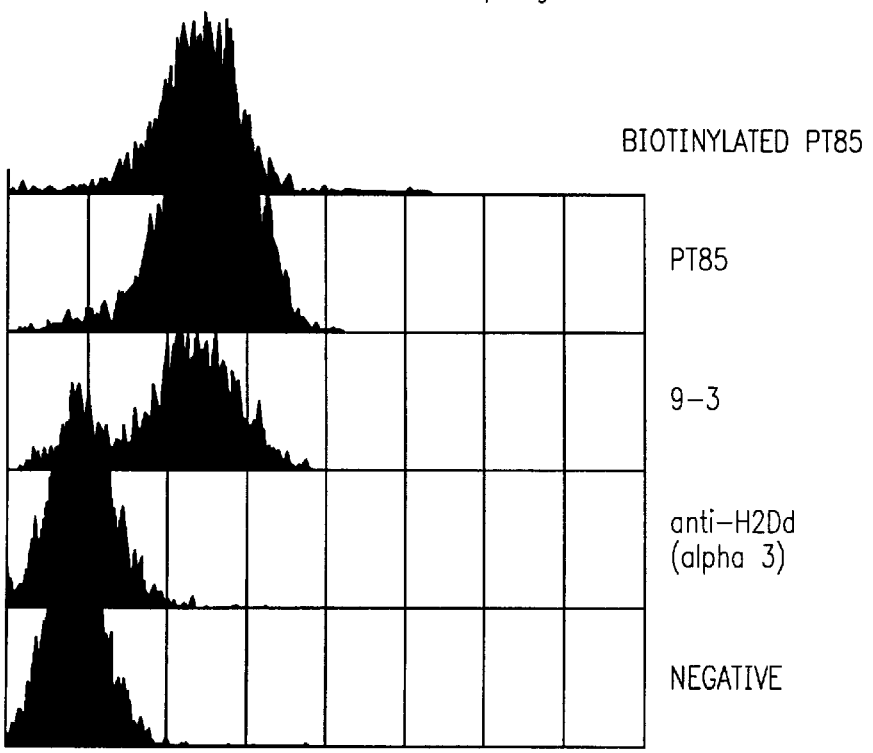
Figure 5E:
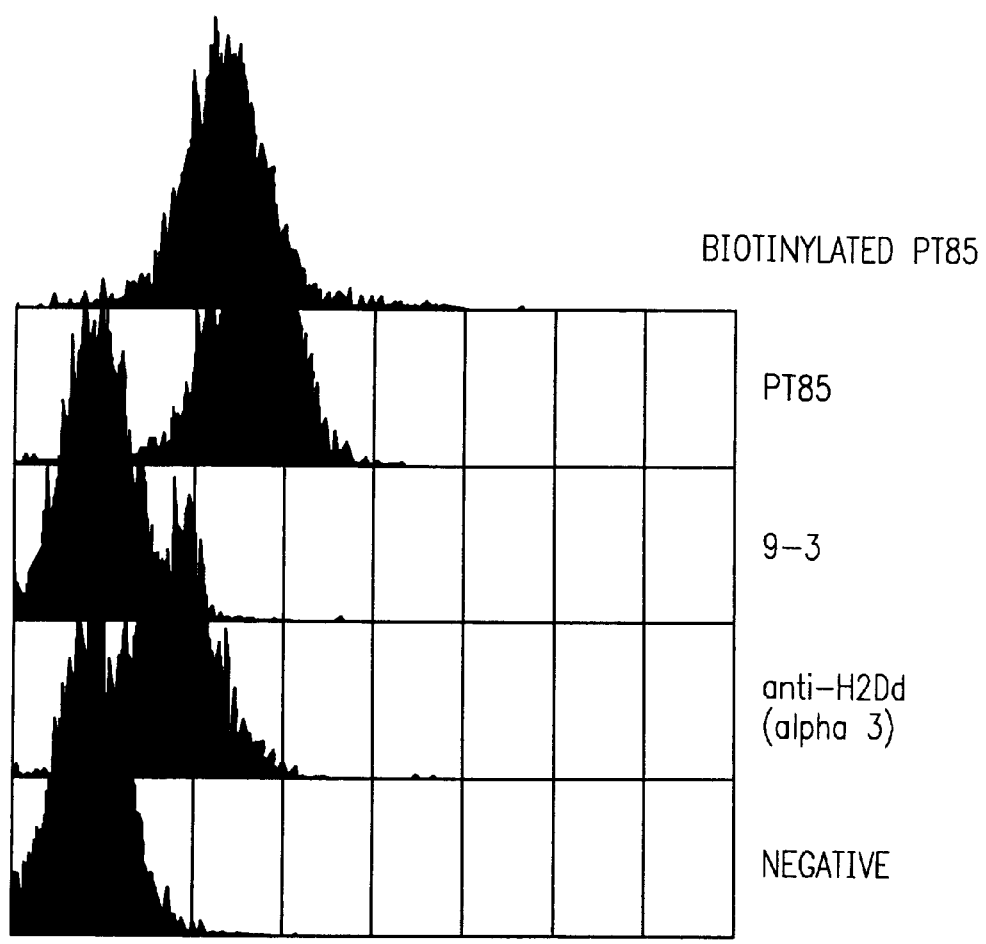

C1498 cells were transfected with recombinant cDNA constructs encoding (a) the leader, α1, α2, transmembrane and cytoplasmic domains of the murine MHC class I polypeptide $H2D^d$ and the α3 domain of the porcine MHC class I polypeptide PD1 (SEQ ID NO:9) (FIG. 4A) and (b) the leader, α3, transmembrane and cytoplasmic domains of $H2D^d$ and the α1 and α2 domains of PD1 (FIG. 4B). Appropriately, antibody 9-3, bound to cells transfected with construct (a) but not to cells transfected with construct (b) (FIG. 5D). Conversely, an antibody that specifically recognizes the α3 domain of $H2D^d$, bound to cells transfected with construct (b) (FIG. 5E). Antibody PT-85 which recognizes a determinant in the α1 or α2 domain of porcine MHC class I polypeptides, bound to cells transfected with construct (b) and not construct (a).

These experiments indicate that wild-type porcine MHC class I polypeptides expressed by an appropriate expression vector in xenogeneic cells assume their normal wild-type conformation. Furthermore, the experiments with the chimeric cDNA constructs indicate that individual domains of MHC class I polypeptides, when associated with other domains from another species, also assume their normal wild-type conformation. The experiments therefore provide evidence that such constructs, when expressed in cells derived from prospective porcine tissue transplant recipients, will produce the proteins in the same 3-dimensional configuration as on porcine tissues to be grafted and thus will be useful for inducing porcine MHC class I polypeptide specific immunological tolerance in the relevant patients.

Example 3

Analysis of the Porcine MHC Class I Sequences

Figure 6A:
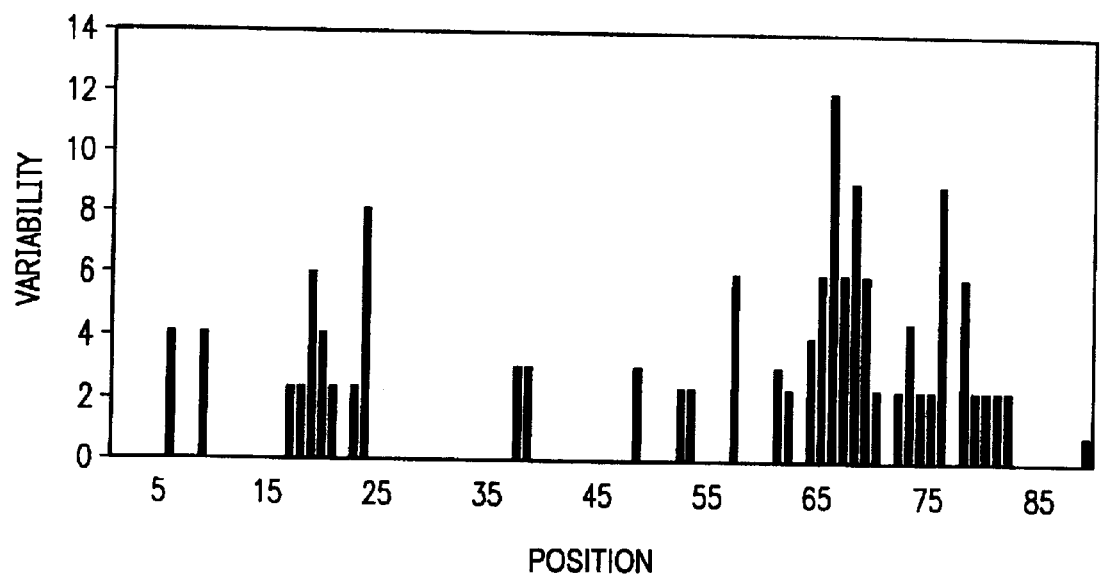
FIGS. 6A and 6B are bar graphs depicting variability plots of the p1 and p14 porcine MHC class I genes. The plots show the greatest degree of polymorphism present within the α1 (FIG. 6A) and α2 (FIG. 6B) domains. The α3 domain was highly conserved among the six genes and is not shown.
Figure 6B:
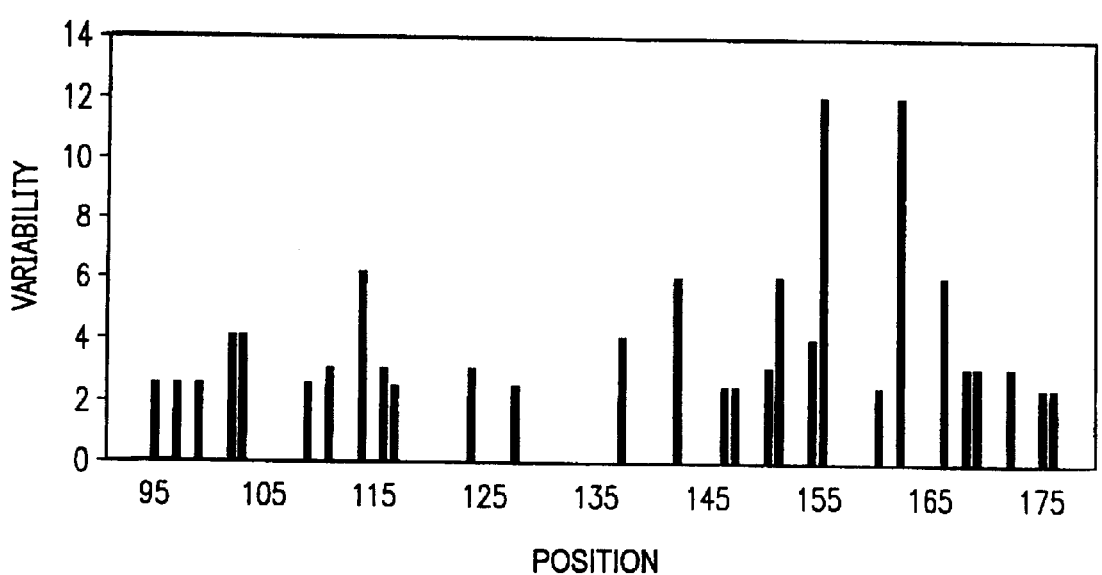

The polymorphic sites in the porcine MHC class I genes were analyzed by variability plots of the individual sequences. The plots (FIGS. 6A and 6B) showed that the greatest degree of polymorphism were within the α1 and α2 domains. The α3 domains differed by a single amino acid in one haplotype. In the α1 domain, the sites of greatest polymorphism corresponded to those seen in the human genes and correlated with the portions of the alpha helix that face the antigen binding groove of the MHC class I molecule; the sites of polymorphism in the α1 domain were clustered at positions 62–79. However, unlike the human genes in which the sites of polymorphism in the α2 domain are predominantly in the β-pleated sheets [Parham et al. (1988) Proc. Natl. Acad. Sci. U.S.A. 85:4005], in the porcine MHC class I genes the regions of greatest polymorphism were in the alpha helical portion of the α2 domain. In the α2 domain, the sites with greatest variability were at positions 156 and 163; the positions that displayed the greatest polymorphism in the α2 domain of HLA [Parham et al. (1988), cited supra], 95, 97, 114 and 116, displayed less variability in porcine MHC class I.

Two additional sites of homology between the porcine and human sequences were conserved among all six genes. The cysteines at positions 101 and 164 and those at 203 and 259 form disulfide bonds in HLA and were present in the porcine sequences. The N-linked glycosylation consensus sequence at positions 86–88 was conserved in all six genes.

The human T cell response against porcine tissue has been shown to occur largely through direct recognition of porcine antigen presenting cells by the human T cells [Yamada et al. (1995) J. Immunol. 155:5249; Murray et al. (1994) Immunity 1:57; Rollins et al. (1994) Transplantation 57:1709], as well as through an indirect mechanism in which porcine antigens are processed and presented to human T cells by human antigen presenting cells [Yamada et al., cited supra]. This indicates that the human T cell receptor can recognize porcine MHC class I polypeptides directly, and human T cells that can kill porcine cells have been demonstrated [Yamada et al., cited supra; Donnelly et al. (1997) Cell. Immunol. 175:171]. An interaction of CD8 molecules on the T cell surface with MHC class I on the target increases the strength of the effector function. Comparison of sequences required for binding of human CD8 to human MHC class I [Salter et al. (1990) Nature 345:41] to the sequences present in the porcine MHC class I genes (FIG. 7A and FIG. 7B) (SEQ ID NOS:16–21 indicates that at least two of the amino acids in the primary binding site were altered: one of these changes (Thr 225->Ser 225) was conservative but a second (Thr 228->Met 228) was nonconservative and may therefore weaken the interaction of human T cells with porcine MHC class I.

Porcine cells have recently been shown to be susceptible to lysis by human NK cells. NK clones are known to be inhibited by MHC class I polypeptides in the autologous situation, and recent studies have elucidated sequences present in MHC class I polypeptides that are recognized by specific receptors on human NK cells and account for resistance to lysis [Gumperz et al. (1995) J. Exp. Med. 181:1133; Colonna et al. (1993) Proc. Natl. Acad. Sci. U.S.A. 90:12000; Biassoni et al. (1995) J. Exp. Med. 182:605; Cella et al. (1994) J. Exp. Med. 180:1235]. In FIG. 8 the known sequences that confer resistance to human NK receptors to the sequences found in the porcine MHC class I molecules (SEQ ID NOS:22–34) are compared; for the group 1 NK clones (FIG. 8A), Lys 80 is the key residue conferring resistance [Biassoni et al., cited supra], whereas for group 2 NK clones (FIG. 8B), Ser 77[Biassoni et al., cited supra] and Asn 80[Mandelboim et al. (1996) J. Exp. Med. 184:913] have both been implicated as the critical amino acid. For HLA-B an Ile at position 80 accounts for binding of the NKB1 receptor and prevents lysis by NK cells that express this receptor [Cella et al., cited supra] (FIG. 8C). In addition, recently reported inhibitory receptors that recognize HLA-A may be inhibited by Asp at position 74[Storkus et al. (1991) Proc. Natl. Acad. Sci. U.S.A. 88:5989; Dohring et al. (1996) J. Immunol. 156:3098], and this residue was not found in the porcine MHC class I sequences. None of the sequences that these negative receptors recognize were present in the porcine molecules characterized in this study except for Asn at position 80 in PC1.

One can create variant porcine MHC class I polypeptides which are more likely to induce NK inhibition by, at the critical positions described above, replacing the naturally-occuring porcine amino acid with a corresponding human MHC class I amino acid, e.g, from HLA-G, thought to be important for inhibition of NK cells. Pazmany et al. [(1996) Science 274:792] and Lanier [(1997) Immunity 6:371] describe HLA residues thought to be important for NK cell interaction.

Example 4

Injection of Mice With Fibroblasts Harboring an Expression Vector

In order to test the utility of the pZeoSV expression vector (Invitrogen) in inducing immunological tolerance, a LacZ gene containing version of pZeoSV (pzeoSVLacZ) was transfected into BALB/c mouse fibroblasts. A clone (Fibro LacZ #4) expressing high levels of LacZ activity was selected for further experimentation. To transplant these cells into blood clots, $10^6$ transfected cells, collected by centrifugation were combined with 100 µl of blood from the recipient mouse. The cell/blood mixture was allowed to clot. Approximately $1\times10^6$ Fibro LacZ #4 cells were grafted in blood clots under the kidney capsules of BALB/c mice. Mice were sacrificed at various times thereafter, their kidneys were removed, sectioned, stained for LacZ activity and counterstained. Kidneys from mice sacrificed on day 0 showed positive LacZ staining only in the blood clot. On the other hand, positive staining in the majority of the kidney was seen in mice sacrificed on day 14. In an identical experiment carried out in nude mice, kidneys obtained from mice sacrificed on day 4 showed staining on the side to which the graft had been applied. Kidneys from nude mice obtained 14 days after grafting showed a larger area of staining. These experiments indicate that fibroblasts harboring an appropriate vector (i) are capable of expressing the gene contained by the vector when injected into the tissue of a mouse and (ii) will colonize such tissues. It seems likely therefore that cells harboring the same expression vector containing a porcine MHC class I gene of the invention would have the same properties and would thereby be useful for inducing immunological tolerance in appropriate mammals, preferably human prospective porcine tissue transplant recipients.

Although the invention has been described with reference to the presently preferred embodiment, it should be understood that various modifications can be made without departing from the spirit of the invention. Accordingly, the invention is limited only by the following claims.

What is claimed is:

1. An isolated nucleic acid molecule comprising the nucleotide sequence of SEQ ID NO:1.

2. A vector comprising the isolated nucleic acid molecule of claim 1.

3. The vector of claim 2 wherein the vector is an expression vector.

4. A cell line containing the isolated nucleic acid molecule of claim 1.

5. A cell line containing the vector of claim 2 or 3.

* * * * *

UNITED STATES PATENT AND TRADEMARK OFFICE
CERTIFICATE OF CORRECTION

PATENT NO. : 6,521,448 B1  Page 1 of 1
DATED : February 18, 2003
INVENTOR(S) : Edge et al.

It is certified that error appears in the above-identified patent and that said Letters Patent is hereby corrected as shown below:

Column 2,
Line 44, delete "$PD_1$" and insert -- PD1 --.

Column 5,
Line 28, delete "pd 1" (first occurrence) and insert -- pcl --.

Column 6,
Line 59, delete "trD" and insert -- trp --.

Column 11,
Line 13, delete "calorimetric" and insert -- colorimetric --.

Column 17,
Line 7, delete "$^1Cr$" and insert -- $^{51}Cr$ --.

Column 18,
Line 49, delete the period (".") after "is".

Column 20,
Line 36, insert -- F: -- at the start of the line beginning with 'Examples'.
Line 54, delete the space after "G" (second occurrence).

Column 21,
Line 50, delete "pd 1" and insert -- pcl --.

Signed and Sealed this

Eighteenth Day of November, 2003

JAMES E. ROGAN
*Director of the United States Patent and Trademark Office*

SEQUENCE LISTING

<160> NUMBER OF SEQ ID NOS: 37

<210> SEQ ID NO 1
<211> LENGTH: 1086
<212> TYPE: DNA
<213> ORGANISM: Sus scrofa
<220> FEATURE:
<221> NAME/KEY: CDS
<222> LOCATION: (1)...(1083)

<400> SEQUENCE: 1

| | | | | | | | | | | | | | | | | |
|---|---|---|---|---|---|---|---|---|---|---|---|---|---|---|---|---|
| atg | ggg | cct | gga | gcc | ctc | ttc | ctg | ctg | ctg | tcg | ggg | acc | ctg | gcc | ctg | 48 |
| Met | Gly | Pro | Gly | Ala | Leu | Phe | Leu | Leu | Leu | Ser | Gly | Thr | Leu | Ala | Leu | |
| 1 | | | | 5 | | | | | 10 | | | | | 15 | | |

| acc | ggg | acc | cag | gcg | ggt | ccc | cac | tcc | ctg | agc | tat | ttc | tac | acc | gcc | 96 |
|---|---|---|---|---|---|---|---|---|---|---|---|---|---|---|---|---|
| Thr | Gly | Thr | Gln | Ala | Gly | Pro | His | Ser | Leu | Ser | Tyr | Phe | Tyr | Thr | Ala | |
| | | | 20 | | | | | 25 | | | | | 30 | | | |

| gtg | tcc | cgg | ccc | gac | cgc | ggg | gag | ccc | ccg | ttc | atc | gcc | gtc | ggc | tac | 144 |
|---|---|---|---|---|---|---|---|---|---|---|---|---|---|---|---|---|
| Val | Ser | Arg | Pro | Asp | Arg | Gly | Glu | Pro | Pro | Phe | Ile | Ala | Val | Gly | Tyr | |
| | | 35 | | | | | 40 | | | | | 45 | | | | |

| gtg | gac | gac | acg | cag | ttc | gtg | cgg | ttc | gac | aac | tac | gcc | ccg | aat | ccg | 192 |
|---|---|---|---|---|---|---|---|---|---|---|---|---|---|---|---|---|
| Val | Asp | Asp | Thr | Gln | Phe | Val | Arg | Phe | Asp | Asn | Tyr | Ala | Pro | Asn | Pro | |
| 50 | | | | | 55 | | | | | 60 | | | | | | |

| cgg | atg | gag | cct | cgg | gtg | ccg | tgg | ata | cag | cag | gag | ggg | cag | gac | tat | 240 |
|---|---|---|---|---|---|---|---|---|---|---|---|---|---|---|---|---|
| Arg | Met | Glu | Pro | Arg | Val | Pro | Trp | Ile | Gln | Gln | Glu | Gly | Gln | Asp | Tyr | |
| 65 | | | | 70 | | | | | 75 | | | | | 80 | | |

| tgg | gat | gag | gag | acg | cgg | aaa | gtc | aag | gac | aac | gca | cag | act | ctc | cga | 288 |
|---|---|---|---|---|---|---|---|---|---|---|---|---|---|---|---|---|
| Trp | Asp | Glu | Glu | Thr | Arg | Lys | Val | Lys | Asp | Asn | Ala | Gln | Thr | Leu | Arg | |
| | | | | 85 | | | | | 90 | | | | | 95 | | |

| gtg | ggc | ctg | aac | acc | ctg | cgc | ggc | tac | tac | aac | cag | agc | gag | gcc | ggg | 336 |
|---|---|---|---|---|---|---|---|---|---|---|---|---|---|---|---|---|
| Val | Gly | Leu | Asn | Thr | Leu | Arg | Gly | Tyr | Tyr | Asn | Gln | Ser | Glu | Ala | Gly | |
| | | | 100 | | | | | 105 | | | | | 110 | | | |

| tct | cac | acc | ctc | cag | agc | atg | ttt | ggc | tgc | tac | ttg | gga | cca | gac | ggg | 384 |
|---|---|---|---|---|---|---|---|---|---|---|---|---|---|---|---|---|
| Ser | His | Thr | Leu | Gln | Ser | Met | Phe | Gly | Cys | Tyr | Leu | Gly | Pro | Asp | Gly | |
| | | 115 | | | | | 120 | | | | | 125 | | | | |

| ctc | ctc | ctc | cac | ggg | tac | aga | cag | gac | gcc | tac | gac | ggc | gcc | gat | tac | 432 |
|---|---|---|---|---|---|---|---|---|---|---|---|---|---|---|---|---|
| Leu | Leu | Leu | His | Gly | Tyr | Arg | Gln | Asp | Ala | Tyr | Asp | Gly | Ala | Asp | Tyr | |
| | 130 | | | | | 135 | | | | | 140 | | | | | |

| atc | gcc | ctg | aac | gag | gac | ctg | cgc | tcc | tgg | acc | gcg | gcg | gac | atg | gcg | 480 |
|---|---|---|---|---|---|---|---|---|---|---|---|---|---|---|---|---|
| Ile | Ala | Leu | Asn | Glu | Asp | Leu | Arg | Ser | Trp | Thr | Ala | Ala | Asp | Met | Ala | |
| 145 | | | | | 150 | | | | | 155 | | | | | 160 | |

| gct | cag | atc | tcc | aag | cgc | aag | tgg | gag | gcg | gcc | gat | gag | gcg | gag | cgg | 528 |
|---|---|---|---|---|---|---|---|---|---|---|---|---|---|---|---|---|
| Ala | Gln | Ile | Ser | Lys | Arg | Lys | Trp | Glu | Ala | Ala | Asp | Glu | Ala | Glu | Arg | |
| | | | | 165 | | | | | 170 | | | | | 175 | | |

| atg | agg | agc | tac | ctg | cag | ggc | cgg | tgt | gtg | gag | ggg | ctc | cgc | aga | tac | 576 |
|---|---|---|---|---|---|---|---|---|---|---|---|---|---|---|---|---|
| Met | Arg | Ser | Tyr | Leu | Gln | Gly | Arg | Cys | Val | Glu | Gly | Leu | Arg | Arg | Tyr | |
| | | | 180 | | | | | 185 | | | | | 190 | | | |

| ctg | cag | atg | ggg | aag | gac | acg | ctg | cag | cgc | gca | gac | cct | cca | aag | aca | 624 |
|---|---|---|---|---|---|---|---|---|---|---|---|---|---|---|---|---|
| Leu | Gln | Met | Gly | Lys | Asp | Thr | Leu | Gln | Arg | Ala | Asp | Pro | Pro | Lys | Thr | |
| | | 195 | | | | | 200 | | | | | 205 | | | | |

| cat | gtg | acc | cgc | cac | ccc | agc | tct | gac | ctg | ggg | gtc | acc | ttg | agg | tgc | 672 |
|---|---|---|---|---|---|---|---|---|---|---|---|---|---|---|---|---|
| His | Val | Thr | Arg | His | Pro | Ser | Ser | Asp | Leu | Gly | Val | Thr | Leu | Arg | Cys | |
| | 210 | | | | | 215 | | | | | 220 | | | | | |

| tgg | gcc | ctg | ggc | ttc | tac | cct | aag | gag | atc | tcc | ctg | acc | tgg | cag | cgc | 720 |
|---|---|---|---|---|---|---|---|---|---|---|---|---|---|---|---|---|
| Trp | Ala | Leu | Gly | Phe | Tyr | Pro | Lys | Glu | Ile | Ser | Leu | Thr | Trp | Gln | Arg | |
| 225 | | | | | 230 | | | | | 235 | | | | | 240 | |

| gag | ggc | cag | gac | cag | agc | cag | gac | atg | gag | ctg | gtg | gag | acc | agg | ccc | 768 |
|---|---|---|---|---|---|---|---|---|---|---|---|---|---|---|---|---|
| Glu | Gly | Gln | Asp | Gln | Ser | Gln | Asp | Met | Glu | Leu | Val | Glu | Thr | Arg | Pro | |
| | | | | 245 | | | | | 250 | | | | | 255 | | |

-continued

```
tca ggg gat ggg acc ttc cag aag tgg gcg gcc ctg gtg gtg cct cct    816
Ser Gly Asp Gly Thr Phe Gln Lys Trp Ala Ala Leu Val Val Pro Pro
        260                 265                 270 gga gag gag cag agc tac acc tgc cat gtg cag cac gag ggc ctg cag    864
Gly Glu Glu Gln Ser Tyr Thr Cys His Val Gln His Glu Gly Leu Gln
            275                 280                 285 gag ccc ctc acc ctg aga tgg gac cct gct cag ccc ccc gtc ccc atg    912
Glu Pro Leu Thr Leu Arg Trp Asp Pro Ala Gln Pro Pro Val Pro Met
290                 295                 300 gtg ggc atc act gtt ggc ctg gtt ctt gtc ctg gtc gct gga gcc atg    960
Val Gly Ile Thr Val Gly Leu Val Leu Val Leu Val Ala Gly Ala Met
305                 310                 315                 320 gtg gct gga gtt gtg atc tgg agg aag acg cgc tca ggt gaa aaa gga   1008
Val Ala Gly Val Val Ile Trp Arg Lys Thr Arg Ser Gly Glu Lys Gly
                325                 330                 335 ggg agc tac act cag gct gca ggc agt gac agt gcc cag ggc tcc gat   1056
Gly Ser Tyr Thr Gln Ala Ala Gly Ser Asp Ser Ala Gln Gly Ser Asp
            340                 345                 350 gtg tcc ctt acc aag gat cct aga gtg tga                           1086
Val Ser Leu Thr Lys Asp Pro Arg Val
        355                 360
```

<210> SEQ ID NO 2
<211> LENGTH: 1086
<212> TYPE: DNA
<213> ORGANISM: Sus scrofa
<220> FEATURE:
<221> NAME/KEY: CDS
<222> LOCATION: (1)...(1083)

<400> SEQUENCE: 2

```
atg ggg cct gga gcc ctc ttc ctg ctg ctg tcg ggg acc ctg gcc ctg     48
Met Gly Pro Gly Ala Leu Phe Leu Leu Leu Ser Gly Thr Leu Ala Leu
1               5                   10                  15 act ggt acc cgg gag ggt ccc cac tcc ctg agg tat ttc gac acc gcc     96
Thr Gly Thr Arg Glu Gly Pro His Ser Leu Arg Tyr Phe Asp Thr Ala
                20                  25                  30 gtg tcc cgg ccc gac cgc agg aag ccc cgt ttc atc tcc gtc ggc tac    144
Val Ser Arg Pro Asp Arg Arg Lys Pro Arg Phe Ile Ser Val Gly Tyr
            35                  40                  45 gtg gac gac acg cag ttc gtg cgg ttc gac agc gac gcc ccc aat ccg    192
Val Asp Asp Thr Gln Phe Val Arg Phe Asp Ser Asp Ala Pro Asn Pro
        50                  55                  60 cgg atg gag ccg cgg gcg ccg tgg ata cag cag gag ggg cag aag tat    240
Arg Met Glu Pro Arg Ala Pro Trp Ile Gln Gln Glu Gly Gln Lys Tyr
65                  70                  75                  80 tgg gat gag gag acg cag aac gcc atg ggc agc gca cag act ttc cga    288
Trp Asp Glu Glu Thr Gln Asn Ala Met Gly Ser Ala Gln Thr Phe Arg
                85                  90                  95 gtg aac ctg aag aac ctg cgc ggc tac tac aac cag agc gag gcc ggg    336
Val Asn Leu Lys Asn Leu Arg Gly Tyr Tyr Asn Gln Ser Glu Ala Gly
            100                 105                 110 tct cac acc ctc cag agc atg tac ggc tgc gac gtg gga cca gac ggg    384
Ser His Thr Leu Gln Ser Met Tyr Gly Cys Asp Val Gly Pro Asp Gly
        115                 120                 125 ctc ttc ctc cgc ggg tac cat cag gac gcc tac gac ggc gcc gat tac    432
Leu Phe Leu Arg Gly Tyr His Gln Asp Ala Tyr Asp Gly Ala Asp Tyr
    130                 135                 140 atc gcc ctg aac gag gac ctg cgc tcc tgg acc gcg gcg gac acg gcg    480
Ile Ala Leu Asn Glu Asp Leu Arg Ser Trp Thr Ala Ala Asp Thr Ala
145                 150                 155                 160
```

-continued

```
gct cag atc gcc aag cgc aag tgg gag gcg gcc gat gtg gct gag cag     528
Ala Gln Ile Ala Lys Arg Lys Trp Glu Ala Ala Asp Val Ala Glu Gln
            165                 170                 175 tgg agg agc tac ctg gag ggc gcg tgt gtg gag tgg ctc cag aaa tac     576
Trp Arg Ser Tyr Leu Glu Gly Ala Cys Val Glu Trp Leu Gln Lys Tyr
        180                 185                 190 ctg gag atg gga aat aac acg ctg cag cgc gca gag cct cca aag aca     624
Leu Glu Met Gly Asn Asn Thr Leu Gln Arg Ala Glu Pro Pro Lys Thr
    195                 200                 205 cat gtg acc cgc cac ccc agc tct gac ctg ggg gtc acc ttg agg tgc     672
His Val Thr Arg His Pro Ser Ser Asp Leu Gly Val Thr Leu Arg Cys
210                 215                 220 tgg gcc ctg ggc ttc tac cct aag gag atc tcc ctg acc tgg cag cgg     720
Trp Ala Leu Gly Phe Tyr Pro Lys Glu Ile Ser Leu Thr Trp Gln Arg
225                 230                 235                 240 gag ggg cag gac cag agc cag gac atg gag ctg gtg gag acc agg ccc     768
Glu Gly Gln Asp Gln Ser Gln Asp Met Glu Leu Val Glu Thr Arg Pro
                245                 250                 255 tca ggg gat ggg acc ttc cag aag tgg gcg gcc ctg gtg gtg cct cct     816
Ser Gly Asp Gly Thr Phe Gln Lys Trp Ala Ala Leu Val Val Pro Pro
            260                 265                 270 gga gag gag cag agc tac acc tgc cat gtg cag cac gag ggc ctg cag     864
Gly Glu Glu Gln Ser Tyr Thr Cys His Val Gln His Glu Gly Leu Gln
        275                 280                 285 gag ccc ctc acc ctg aga tgg gac cct cct cag ccc ccc gtc ccc atc     912
Glu Pro Leu Thr Leu Arg Trp Asp Pro Pro Gln Pro Pro Val Pro Ile
    290                 295                 300 gtg ggc atc att gtt ggc ctg gtt ctc gtc ctg gtc act gga gcc gtg     960
Val Gly Ile Ile Val Gly Leu Val Leu Val Leu Val Thr Gly Ala Val
305                 310                 315                 320 gtg gct gga gtt gtg atc tgg agg aag aag cgc tca ggt gaa aaa gga    1008
Val Ala Gly Val Val Ile Trp Arg Lys Lys Arg Ser Gly Glu Lys Gly
                325                 330                 335 ggg agc tac act cag gct gca ggc agt gac agt gcc cag ggc tct gat    1056
Gly Ser Tyr Thr Gln Ala Ala Gly Ser Asp Ser Ala Gln Gly Ser Asp
            340                 345                 350 gtg tcc ctt acc aag gat cct aga gtg tga                            1086
Val Ser Leu Thr Lys Asp Pro Arg Val
        355                 360
```

<210> SEQ ID NO 3
<211> LENGTH: 1086
<212> TYPE: DNA
<213> ORGANISM: Sus scrofa
<220> FEATURE:
<221> NAME/KEY: CDS
<222> LOCATION: (1)...(1083)

<400> SEQUENCE: 3

```
atg ggg cct gga gcc ctc ttc ctg ctg ctg tcg ggg acc ctg gcc ctg      48
Met Gly Pro Gly Ala Leu Phe Leu Leu Leu Ser Gly Thr Leu Ala Leu
1               5                   10                  15 acc ggg acc cag gcg ggt ccc cac tcc ctg agc tat ttc tac acc gcc      96
Thr Gly Thr Gln Ala Gly Pro His Ser Leu Ser Tyr Phe Tyr Thr Ala
            20                  25                  30 gtg tcc cgg ccc gac cgc ggg gac tct cgc ttc atc gcc gtc ggc tac     144
Val Ser Arg Pro Asp Arg Gly Asp Ser Arg Phe Ile Ala Val Gly Tyr
        35                  40                  45 gtg gac gac acg cag ttc gtg cgg ttc gac aac tac gcc ccg aat ccg     192
Val Asp Asp Thr Gln Phe Val Arg Phe Asp Asn Tyr Ala Pro Asn Pro
    50                  55                  60
```

-continued

```
cgg atg gag cct cgg gtg ccg tgg ata cag cag gag ggg cag gag tat       240
Arg Met Glu Pro Arg Val Pro Trp Ile Gln Gln Glu Gly Gln Glu Tyr
 65                  70                  75                  80 tgg gat cgg gag acg cgg aat gtc aag gaa acc gca cag act tac gga       288
Trp Asp Arg Glu Thr Arg Asn Val Lys Glu Thr Ala Gln Thr Tyr Gly
                 85                  90                  95 gtg ggc ctg aac acc ctg cgc ggc tac tac aac cag agc gag gcc ggg       336
Val Gly Leu Asn Thr Leu Arg Gly Tyr Tyr Asn Gln Ser Glu Ala Gly
            100                 105                 110 tct cac acc ctc cag agc atg tac ggc tgc tac ttg gga cca gac ggg       384
Ser His Thr Leu Gln Ser Met Tyr Gly Cys Tyr Leu Gly Pro Asp Gly
        115                 120                 125 ctc ctc ctc cac ggg tac aga cag gac gcc tac gac ggc gcc gat tac       432
Leu Leu Leu His Gly Tyr Arg Gln Asp Ala Tyr Asp Gly Ala Asp Tyr
    130                 135                 140 atc gcc ctg aac gag gac ctg cgc tcc tgg acc gcg gcg gac atg gcg       480
Ile Ala Leu Asn Glu Asp Leu Arg Ser Trp Thr Ala Ala Asp Met Ala
145                 150                 155                 160 gct cag atc acc aag cgc aag tgg gag gcg gcc gat gag gcg gag cgt       528
Ala Gln Ile Thr Lys Arg Lys Trp Glu Ala Ala Asp Glu Ala Glu Arg
                165                 170                 175 agg agg agc tac ctg cag gga ctg tgt gtg gag tcg ctc cgc aga tac       576
Arg Arg Ser Tyr Leu Gln Gly Leu Cys Val Glu Ser Leu Arg Arg Tyr
            180                 185                 190 ctg gag atg ggg aag gac acg ctg cag cgc gca gag cct cca aag aca       624
Leu Glu Met Gly Lys Asp Thr Leu Gln Arg Ala Glu Pro Pro Lys Thr
        195                 200                 205 cat gtg acc cgc cac ccc agc tct gac ctc ggg gtc acc ttg agg tgc       672
His Val Thr Arg His Pro Ser Ser Asp Leu Gly Val Thr Leu Arg Cys
    210                 215                 220 tgg gcc ctg ggc ttc tac cct aag gag atc tcc ctg acc tgg cag cgg       720
Trp Ala Leu Gly Phe Tyr Pro Lys Glu Ile Ser Leu Thr Trp Gln Arg
225                 230                 235                 240 gag ggc cag gac cag agc cag gac atg gag ctg gtg gag acc agg ccc       768
Glu Gly Gln Asp Gln Ser Gln Asp Met Glu Leu Val Glu Thr Arg Pro
                245                 250                 255 tca ggg gat ggg acc ttc cag aag tgg gcg gcc ctg gtg gtg cct cct       816
Ser Gly Asp Gly Thr Phe Gln Lys Trp Ala Ala Leu Val Val Pro Pro
            260                 265                 270 gga gag gag cag agc tac acc tgc cat gtg cag cac gag ggc ctg cag       864
Gly Glu Glu Gln Ser Tyr Thr Cys His Val Gln His Glu Gly Leu Gln
        275                 280                 285 gag ccc ctc acc ctg aga tgg gac cct gct cag ccc ccc gtc ccc atc       912
Glu Pro Leu Thr Leu Arg Trp Asp Pro Ala Gln Pro Pro Val Pro Ile
    290                 295                 300 gtg ggc atc att gtt ggc ctg gtt ctg gtc ctg gtc gct gga gcc atg       960
Val Gly Ile Ile Val Gly Leu Val Leu Val Leu Val Ala Gly Ala Met
305                 310                 315                 320 gtg gct gga gtt gtg atc tgg agg aag acg cgc tca ggt gaa aaa gga      1008
Val Ala Gly Val Val Ile Trp Arg Lys Thr Arg Ser Gly Glu Lys Gly
                325                 330                 335 ggg agc tac act cag gct gca ggc agt gac agt gac cag ggc tcc gat      1056
Gly Ser Tyr Thr Gln Ala Ala Gly Ser Asp Ser Asp Gln Gly Ser Asp
            340                 345                 350 gtg tcc ctt acc aag gat cct aga gtg tga                              1086
Val Ser Leu Thr Lys Asp Pro Arg Val
        355                 360
```

<210> SEQ ID NO 4
<211> LENGTH: 1095

```
<212> TYPE: DNA
<213> ORGANISM: Sus scrofa
<220> FEATURE:
<221> NAME/KEY: CDS
<222> LOCATION: (1)...(1092)

<400> SEQUENCE: 4 atg cgg gtc aga ggc cct caa gcc atc ctc att ctg ctg tcg ggg gcc         48
Met Arg Val Arg Gly Pro Gln Ala Ile Leu Ile Leu Leu Ser Gly Ala
 1               5                  10                  15 ctg gcc ctg acc ggg acc cgg gcg ggt ccc cac tcc ctg agg tat ttc         96
Leu Ala Leu Thr Gly Thr Arg Ala Gly Pro His Ser Leu Arg Tyr Phe
             20                  25                  30 gac acc gcc gtg tcc cgg ccc gac cgc ggg gac tcc cgc ttc ctc acc        144
Asp Thr Ala Val Ser Arg Pro Asp Arg Gly Asp Ser Arg Phe Leu Thr
         35                  40                  45 gtc ggc tac gtg gac gac acg cag ttc gtg agg ttc gac agc gac gcc        192
Val Gly Tyr Val Asp Asp Thr Gln Phe Val Arg Phe Asp Ser Asp Ala
     50                  55                  60 ccg aat ccg agg gag gag ccg cgg gcg ccg tgg ata cag cag gag ggg        240
Pro Asn Pro Arg Glu Glu Pro Arg Ala Pro Trp Ile Gln Gln Glu Gly
 65                  70                  75                  80 cag gac tat tgg gat cgg gag aca cag atc agc aag gaa acc gca cag        288
Gln Asp Tyr Trp Asp Arg Glu Thr Gln Ile Ser Lys Glu Thr Ala Gln
                 85                  90                  95 act tac cga gtg gac ctg aac acc ctg cgc agc tac tac aac cag agc        336
Thr Tyr Arg Val Asp Leu Asn Thr Leu Arg Ser Tyr Tyr Asn Gln Ser
            100                 105                 110 gag gcc ggg tct cac acc ctc cag agc atg tac ggc tgc gac gtg ggg        384
Glu Ala Gly Ser His Thr Leu Gln Ser Met Tyr Gly Cys Asp Val Gly
        115                 120                 125 cca gac ggg ctc ttc ctc cgc ggg tac agt cag ttt ggc tac gac ggc        432
Pro Asp Gly Leu Phe Leu Arg Gly Tyr Ser Gln Phe Gly Tyr Asp Gly
    130                 135                 140 gcc gat tac ctc gcc ctg aac gag gac ctg cgc tcc tgg acc gcg gcg        480
Ala Asp Tyr Leu Ala Leu Asn Glu Asp Leu Arg Ser Trp Thr Ala Ala
145                 150                 155                 160 gac acg gcg gct cag atc tcc aag cgc aag ttt gat gca gcc aat gtg        528
Asp Thr Ala Ala Gln Ile Ser Lys Arg Lys Phe Asp Ala Ala Asn Val
                165                 170                 175 gcg gag cag gag agg agc tac ctg cag ggc ctg tgt gtg gag ggg ctc        576
Ala Glu Gln Glu Arg Ser Tyr Leu Gln Gly Leu Cys Val Glu Gly Leu
            180                 185                 190 cgc aga tac ctg gag atg ggg aag gac acg ctg cag cgc gca gag cct        624
Arg Arg Tyr Leu Glu Met Gly Lys Asp Thr Leu Gln Arg Ala Glu Pro
        195                 200                 205 cca aag aca cat gtg acc cgc cac ccc agc tct gac ctg ggg gtc acc        672
Pro Lys Thr His Val Thr Arg His Pro Ser Ser Asp Leu Gly Val Thr
    210                 215                 220 ttg agg tgc tgg gcc ctg ggc ttc tac cct aag gag atc tcc ctg acc        720
Leu Arg Cys Trp Ala Leu Gly Phe Tyr Pro Lys Glu Ile Ser Leu Thr
225                 230                 235                 240 tgg cag cgg gag ggc cag gac cag agc cag gac atg gag ctg gtg gag        768
Trp Gln Arg Glu Gly Gln Asp Gln Ser Gln Asp Met Glu Leu Val Glu
                245                 250                 255 acc agg ccc tca ggg gat ggg acc ttc cag aag tgg gcg gcc ctg gtg        816
Thr Arg Pro Ser Gly Asp Gly Thr Phe Gln Lys Trp Ala Ala Leu Val
            260                 265                 270 gtg cct cct gga gag gag cag agc tac acc tgc cat gtg cag cac gag        864
Val Pro Pro Gly Glu Glu Gln Ser Tyr Thr Cys His Val Gln His Glu
        275                 280                 285
```

-continued

```
ggc ctg cag gag ccc ctc acc ctg aga tgg gaa cct cca cag ccc ccc       912
Gly Leu Gln Glu Pro Leu Thr Leu Arg Trp Glu Pro Pro Gln Pro Pro
            290                 295                 300 gtc ccc atc gtg ggc atc ttt gtt ggc ctg gtt ctc gtc ctg gtc gct       960
Val Pro Ile Val Gly Ile Phe Val Gly Leu Val Leu Val Leu Val Ala
305                 310                 315                 320 gga acc atg gtg act gga gtt gtg atc tgg agg aag aag cgc tca ggt      1008
Gly Thr Met Val Thr Gly Val Val Ile Trp Arg Lys Lys Arg Ser Gly
                325                 330                 335 gaa aaa gga ggg agc tac act cag gct gca ggg agt gac agt gcc cag      1056
Glu Lys Gly Gly Ser Tyr Thr Gln Ala Ala Gly Ser Asp Ser Ala Gln
            340                 345                 350 ggc tcc gat gtg tcc ctt acc aag gat cct aga gtg tga                  1095
Gly Ser Asp Val Ser Leu Thr Lys Asp Pro Arg Val
            355                 360

<210> SEQ ID NO 5
<211> LENGTH: 1095
<212> TYPE: DNA
<213> ORGANISM: Sus scrofa
<220> FEATURE:
<221> NAME/KEY: CDS
<222> LOCATION: (1)...(1092)

<400> SEQUENCE: 5 atg cgg gtc aga ggc cct caa gcc atc ctc att ctg ctg tcg ggg gcc        48
Met Arg Val Arg Gly Pro Gln Ala Ile Leu Ile Leu Leu Ser Gly Ala
1               5                  10                  15 ctg gcc ctg acc ggg acc cgg gcg ggt ccc cac tcc ctg agc tat ttc        96
Leu Ala Leu Thr Gly Thr Arg Ala Gly Pro His Ser Leu Ser Tyr Phe
            20                  25                  30 tac acc gcc gtg tcc cgg ccc gac ctc ggg gac tcc cgc ttc atc gcc       144
Tyr Thr Ala Val Ser Arg Pro Asp Leu Gly Asp Ser Arg Phe Ile Ala
        35                  40                  45 gtc ggc tac gtg gac gac acg cag ttc gtg cgg ttc gac agc gac gcc       192
Val Gly Tyr Val Asp Asp Thr Gln Phe Val Arg Phe Asp Ser Asp Ala
50                  55                  60 ccg aat ccg cgg atg gag ccg cgg gcg ccg tgg ata gag aag gag ggg       240
Pro Asn Pro Arg Met Glu Pro Arg Ala Pro Trp Ile Glu Lys Glu Gly
65                  70                  75                  80 cag gag tat tgg gat cgg gag aca cag ata caa agg gac acc tca cag       288
Gln Glu Tyr Trp Asp Arg Glu Thr Gln Ile Gln Arg Asp Thr Ser Gln
                85                  90                  95 act tac cga gtg gac ctg aag acc ctg cgc ggc tac tac aac cag agc       336
Thr Tyr Arg Val Asp Leu Lys Thr Leu Arg Gly Tyr Tyr Asn Gln Ser
            100                 105                 110 gag gcc ggg tct cac acc ctc cag agc atg tac ggc tgc tac ttg gga       384
Glu Ala Gly Ser His Thr Leu Gln Ser Met Tyr Gly Cys Tyr Leu Gly
        115                 120                 125 cca gac ggg ctc ctc ctc cgc ggg tac aga cag ttc gcc tac gac ggc       432
Pro Asp Gly Leu Leu Leu Arg Gly Tyr Arg Gln Phe Ala Tyr Asp Gly
130                 135                 140 gcc gat tac ctc gcc ctg aac gag gac ctg cgc tcc tgg acc gcg gcg       480
Ala Asp Tyr Leu Ala Leu Asn Glu Asp Leu Arg Ser Trp Thr Ala Ala
145                 150                 155                 160 gac atg gcg gct cag atc tcc aag cgc aag tgg gag gcg gcc aat gcg       528
Asp Met Ala Ala Gln Ile Ser Lys Arg Lys Trp Glu Ala Ala Asn Ala
                165                 170                 175 gcg gag cag gag agg agc tac ctg cag ggc cgg tgt gtg gag tgg ctc       576
Ala Glu Gln Glu Arg Ser Tyr Leu Gln Gly Arg Cys Val Glu Trp Leu
            180                 185                 190
```

```
cgc aga tac ctg gag atg ggg aag gac acg ctg cag cgc gca gag cct      624
Arg Arg Tyr Leu Glu Met Gly Lys Asp Thr Leu Gln Arg Ala Glu Pro
        195                 200                 205 cca aag aca cat gtg acc cgc cac ccc agc tct gac ctg ggg gtc acc      672
Pro Lys Thr His Val Thr Arg His Pro Ser Ser Asp Leu Gly Val Thr
    210                 215                 220 ttg agg tgc tgg gcc ctg ggc ttc tac cct aag gag atc tcc ctg acc      720
Leu Arg Cys Trp Ala Leu Gly Phe Tyr Pro Lys Glu Ile Ser Leu Thr
225                 230                 235                 240 tgg cag cgc gag ggc cag gac cag agc cag gac atg gag ctg gtg gag      768
Trp Gln Arg Glu Gly Gln Asp Gln Ser Gln Asp Met Glu Leu Val Glu
                245                 250                 255 acc agg ccc tca ggg gat ggg acc ttc cag aag tgg gcg gcc ctg gtg      816
Thr Arg Pro Ser Gly Asp Gly Thr Phe Gln Lys Trp Ala Ala Leu Val
            260                 265                 270 gtg cct cct gga gag gag cag agc tac acc tgc cat gtg cag cac gag      864
Val Pro Pro Gly Glu Glu Gln Ser Tyr Thr Cys His Val Gln His Glu
        275                 280                 285 ggc ctg cag gag ccc ctc acc ctg aga tgg gac cct cct cag ccc ccc      912
Gly Leu Gln Glu Pro Leu Thr Leu Arg Trp Asp Pro Pro Gln Pro Pro
    290                 295                 300 gtc ccc atc gtg ggc atc att gtt ggc ctg gtt ctc gtc ctg gtc gct      960
Val Pro Ile Val Gly Ile Ile Val Gly Leu Val Leu Val Leu Val Ala
305                 310                 315                 320 gga gcc atg gtg gct gga gtt gtg atc tgg agg aag aag cgc tca ggt     1008
Gly Ala Met Val Ala Gly Val Val Ile Trp Arg Lys Lys Arg Ser Gly
                325                 330                 335 gaa aaa gga ggg agc tac act cag gct gca ggc agt gac agt gcc cag     1056
Glu Lys Gly Gly Ser Tyr Thr Gln Ala Ala Gly Ser Asp Ser Ala Gln
            340                 345                 350 ggc tcc gat gtg tcc ctt acc aag gat cct aga gtg tga                 1095
Gly Ser Asp Val Ser Leu Thr Lys Asp Pro Arg Val
        355                 360

<210> SEQ ID NO 6
<211> LENGTH: 1095
<212> TYPE: DNA
<213> ORGANISM: Sus scrofa
<220> FEATURE:
<221> NAME/KEY: CDS
<222> LOCATION: (1)...(1092)

<400> SEQUENCE: 6 atg cgg gtc aga ggc cct caa gcc atc ctc att ctg ctg tcg ggg gcc       48
Met Arg Val Arg Gly Pro Gln Ala Ile Leu Ile Leu Leu Ser Gly Ala
1               5                   10                  15 ctg gcc ctg acc ggg acc cag gcg ggt ccc cac tcc ctg agg tat ttc       96
Leu Ala Leu Thr Gly Thr Gln Ala Gly Pro His Ser Leu Arg Tyr Phe
            20                  25                  30 gac acc gcc gtg tcc cgg ccc gac cgc ggg gag ccc cgt ttc atc gaa      144
Asp Thr Ala Val Ser Arg Pro Asp Arg Gly Glu Pro Arg Phe Ile Glu
        35                  40                  45 gtc ggc tac gtg gac gac acg cag ttc gtg cgg ttc gac agc gac gcc      192
Val Gly Tyr Val Asp Asp Thr Gln Phe Val Arg Phe Asp Ser Asp Ala
    50                  55                  60 ccg aat ccg cgg atg gag cct cgg gcg cgg tgg ata cag cag gag ggg      240
Pro Asn Pro Arg Met Glu Pro Arg Ala Arg Trp Ile Gln Gln Glu Gly
65                  70                  75                  80 cag gag tat tgg gat agg aac acg cgg aac gcc atg ggc aac gca cag      288
Gln Glu Tyr Trp Asp Arg Asn Thr Arg Asn Ala Met Gly Asn Ala Gln
                85                  90                  95
```

-continued

```
att tac cga ggg aac ctg cgc aca gct ctc ggc tac tac aac cag agc      336
Ile Tyr Arg Gly Asn Leu Arg Thr Ala Leu Gly Tyr Tyr Asn Gln Ser
            100                 105                 110 gag gcc ggg tct cac acc atc cag atc atg tac ggc tgc gac gtg gga      384
Glu Ala Gly Ser His Thr Ile Gln Ile Met Tyr Gly Cys Asp Val Gly
        115                 120                 125 cca gac ggg ctc ctc ctc cgc ggg tac agt cag gac gcc tac gac ggc      432
Pro Asp Gly Leu Leu Leu Arg Gly Tyr Ser Gln Asp Ala Tyr Asp Gly
    130                 135                 140 gcc gat tac atc gcc ctg aac gag gac ctg cgc tcc tgg acc gcg gcg      480
Ala Asp Tyr Ile Ala Leu Asn Glu Asp Leu Arg Ser Trp Thr Ala Ala
145                 150                 155                 160 gac acg gcg gct cag atc acc aag cgc aag tgg gag gcg gcc gat gag      528
Asp Thr Ala Ala Gln Ile Thr Lys Arg Lys Trp Glu Ala Ala Asp Glu
                165                 170                 175 gcg gag cgt agg agg agc tac ctg cag ggc acg tgt gtg gag tgg ctc      576
Ala Glu Arg Arg Arg Ser Tyr Leu Gln Gly Thr Cys Val Glu Trp Leu
            180                 185                 190 cag aaa tac ctg cag atg ggg aag gac acg ctg cag cgc gca gag cct      624
Gln Lys Tyr Leu Gln Met Gly Lys Asp Thr Leu Gln Arg Ala Glu Pro
        195                 200                 205 cca aag aca cat gtg acc cgc cac ccc agc tct gac ctc ggg gtc acc      672
Pro Lys Thr His Val Thr Arg His Pro Ser Ser Asp Leu Gly Val Thr
    210                 215                 220 ttg agg tgc tgg gcc ctg ggc ttc tac cct aag gag atc tcc ctg acc      720
Leu Arg Cys Trp Ala Leu Gly Phe Tyr Pro Lys Glu Ile Ser Leu Thr
225                 230                 235                 240 tgg cag cgg gag ggc cag gac cag agc cag gac atg gag ctc gtg gag      768
Trp Gln Arg Glu Gly Gln Asp Gln Ser Gln Asp Met Glu Leu Val Glu
                245                 250                 255 acc agg ccc tca ggg gat ggg acc ttc cag aaa tgg gcg gcc ctg gtg      816
Thr Arg Pro Ser Gly Asp Gly Thr Phe Gln Lys Trp Ala Ala Leu Val
            260                 265                 270 gtg cca cct gga gag gag cag agc tac acc tgc cat gtg cag cat gag      864
Val Pro Pro Gly Glu Glu Gln Ser Tyr Thr Cys His Val Gln His Glu
        275                 280                 285 ggc ctg cag gag cca ctc acc ctg aga tgg gac cct cct cag ccc cct      912
Gly Leu Gln Glu Pro Leu Thr Leu Arg Trp Asp Pro Pro Gln Pro Pro
    290                 295                 300 gtc ccc atc gtg ggc atc att gtt ggc ctg gtt ctg gtc ctg gtc gct      960
Val Pro Ile Val Gly Ile Ile Val Gly Leu Val Leu Val Leu Val Ala
305                 310                 315                 320 gga gcc gtg gtg gct gga gtt gtg atc tgg agg aag aag cgc tca ggt     1008
Gly Ala Val Val Ala Gly Val Val Ile Trp Arg Lys Lys Arg Ser Gly
                325                 330                 335 gaa aaa gga ggg agc tac act cag gct gca ggc agt gac agt gcc cag     1056
Glu Lys Gly Gly Ser Tyr Thr Gln Ala Ala Gly Ser Asp Ser Ala Gln
            340                 345                 350 ggc tcc gat gtg tcc ctt acc aag gat cct aga gtg tga                 1095
Gly Ser Asp Val Ser Leu Thr Lys Asp Pro Arg Val
        355                 360
```

<210> SEQ ID NO 7
<211> LENGTH: 361
<212> TYPE: PRT
<213> ORGANISM: Sus scrofa

<400> SEQUENCE: 7

```
Met Gly Pro Gly Ala Leu Phe Leu Leu Leu Ser Gly Thr Leu Ala Leu
  1               5                  10                  15
```

```
Thr Gly Thr Gln Ala Gly Pro His Ser Leu Ser Tyr Phe Tyr Thr Ala
            20                  25                  30

Val Ser Arg Pro Asp Arg Gly Glu Pro Pro Phe Ile Ala Val Gly Tyr
        35                  40                  45

Val Asp Asp Thr Gln Phe Val Arg Phe Asp Asn Tyr Ala Pro Asn Pro
    50                  55                  60

Arg Met Glu Pro Arg Val Pro Trp Ile Gln Glu Gly Gln Asp Tyr
65                  70                  75                  80

Trp Asp Glu Glu Thr Arg Lys Val Lys Asp Asn Ala Gln Thr Leu Arg
                85                  90                  95

Val Gly Leu Asn Thr Leu Arg Gly Tyr Tyr Asn Gln Ser Glu Ala Gly
            100                 105                 110

Ser His Thr Leu Gln Ser Met Phe Gly Cys Tyr Leu Gly Pro Asp Gly
        115                 120                 125

Leu Leu Leu His Gly Tyr Arg Gln Asp Ala Tyr Asp Gly Ala Asp Tyr
    130                 135                 140

Ile Ala Leu Asn Glu Asp Leu Arg Ser Trp Thr Ala Ala Asp Met Ala
145                 150                 155                 160

Ala Gln Ile Ser Lys Arg Lys Trp Glu Ala Ala Asp Glu Ala Glu Arg
                165                 170                 175

Met Arg Ser Tyr Leu Gln Gly Arg Cys Val Glu Gly Leu Arg Arg Tyr
            180                 185                 190

Leu Gln Met Gly Lys Asp Thr Leu Gln Arg Ala Asp Pro Pro Lys Thr
        195                 200                 205

His Val Thr Arg His Pro Ser Ser Asp Leu Gly Val Thr Leu Arg Cys
    210                 215                 220

Trp Ala Leu Gly Phe Tyr Pro Lys Glu Ile Ser Leu Thr Trp Gln Arg
225                 230                 235                 240

Glu Gly Gln Asp Gln Ser Gln Asp Met Glu Leu Val Glu Thr Arg Pro
                245                 250                 255

Ser Gly Asp Gly Thr Phe Gln Lys Trp Ala Ala Leu Val Val Pro Pro
            260                 265                 270

Gly Glu Glu Gln Ser Tyr Thr Cys His Val Gln His Glu Gly Leu Gln
        275                 280                 285

Glu Pro Leu Thr Leu Arg Trp Asp Pro Ala Gln Pro Pro Val Pro Met
    290                 295                 300

Val Gly Ile Thr Val Gly Leu Val Leu Val Leu Val Ala Gly Ala Met
305                 310                 315                 320

Val Ala Gly Val Val Ile Trp Arg Lys Thr Arg Ser Gly Glu Lys Gly
                325                 330                 335

Gly Ser Tyr Thr Gln Ala Ala Gly Ser Asp Ser Ala Gln Gly Ser Asp
            340                 345                 350

Val Ser Leu Thr Lys Asp Pro Arg Val
        355                 360

<210> SEQ ID NO 8
<211> LENGTH: 361
<212> TYPE: PRT
<213> ORGANISM: Sus scrofa

<400> SEQUENCE: 8

Met Gly Pro Gly Ala Leu Phe Leu Leu Leu Ser Gly Thr Leu Ala Leu
1               5                   10                  15

Thr Gly Thr Arg Glu Gly Pro His Ser Leu Arg Tyr Phe Asp Thr Ala
```

-continued

```
                    20                  25                  30
Val Ser Arg Pro Asp Arg Arg Lys Pro Arg Phe Ile Ser Val Gly Tyr
                35                  40                  45
Val Asp Thr Gln Phe Val Arg Phe Asp Ser Asp Ala Pro Asn Pro
        50                  55                  60
Arg Met Glu Pro Arg Ala Pro Trp Ile Gln Gln Glu Gly Gln Lys Tyr
65                  70                  75                  80
Trp Asp Glu Glu Thr Gln Asn Ala Met Gly Ser Ala Gln Thr Phe Arg
                85                  90                  95
Val Asn Leu Lys Asn Leu Arg Gly Tyr Tyr Asn Gln Ser Glu Ala Gly
                100                 105                 110
Ser His Thr Leu Gln Ser Met Tyr Gly Cys Asp Val Gly Pro Asp Gly
                115                 120                 125
Leu Phe Leu Arg Gly Tyr His Gln Asp Ala Tyr Asp Gly Ala Asp Tyr
                130                 135                 140
Ile Ala Leu Asn Glu Asp Leu Arg Ser Trp Thr Ala Ala Asp Thr Ala
145                 150                 155                 160
Ala Gln Ile Ala Lys Arg Lys Trp Glu Ala Ala Asp Val Ala Glu Gln
                165                 170                 175
Trp Arg Ser Tyr Leu Glu Gly Ala Cys Val Glu Trp Leu Gln Lys Tyr
                180                 185                 190
Leu Glu Met Gly Asn Asn Thr Leu Gln Arg Ala Glu Pro Pro Lys Thr
                195                 200                 205
His Val Thr Arg His Pro Ser Ser Asp Leu Gly Val Thr Leu Arg Cys
            210                 215                 220
Trp Ala Leu Gly Phe Tyr Pro Lys Glu Ile Ser Leu Thr Trp Gln Arg
225                 230                 235                 240
Glu Gly Gln Asp Gln Ser Gln Asp Met Glu Leu Val Glu Thr Arg Pro
                245                 250                 255
Ser Gly Asp Gly Thr Phe Gln Lys Trp Ala Ala Leu Val Val Pro Pro
                260                 265                 270
Gly Glu Glu Gln Ser Tyr Thr Cys His Val Gln His Glu Gly Leu Gln
                275                 280                 285
Glu Pro Leu Thr Leu Arg Trp Asp Pro Pro Gln Pro Val Pro Ile
            290                 295                 300
Val Gly Ile Ile Val Gly Leu Val Leu Val Thr Gly Ala Val
305                 310                 315                 320
Val Ala Gly Val Val Ile Trp Arg Lys Lys Arg Ser Gly Glu Lys Gly
                325                 330                 335
Gly Ser Tyr Thr Gln Ala Ala Gly Ser Asp Ser Ala Gln Gly Ser Asp
                340                 345                 350
Val Ser Leu Thr Lys Asp Pro Arg Val
                355                 360

<210> SEQ ID NO 9
<211> LENGTH: 361
<212> TYPE: PRT
<213> ORGANISM: Sus scrofa

<400> SEQUENCE: 9

Met Gly Pro Gly Ala Leu Phe Leu Leu Leu Ser Gly Thr Leu Ala Leu
1               5                   10                  15
Thr Gly Thr Gln Ala Gly Pro His Ser Leu Ser Tyr Phe Tyr Thr Ala
                20                  25                  30
```

```
Val Ser Arg Pro Asp Arg Gly Asp Ser Arg Phe Ile Ala Val Gly Tyr
         35                  40                  45

Val Asp Asp Thr Gln Phe Val Arg Phe Asp Asn Tyr Ala Pro Asn Pro
         50                  55                  60

Arg Met Glu Pro Arg Val Pro Trp Ile Gln Gln Gly Gln Glu Tyr
 65              70                  75                  80

Trp Asp Arg Glu Thr Arg Asn Val Lys Glu Thr Ala Gln Thr Tyr Gly
                 85                  90                  95

Val Gly Leu Asn Thr Leu Arg Gly Tyr Tyr Asn Gln Ser Glu Ala Gly
                100                 105                 110

Ser His Thr Leu Gln Ser Met Tyr Gly Cys Tyr Leu Gly Pro Asp Gly
            115                 120                 125

Leu Leu Leu His Gly Tyr Arg Gln Asp Ala Tyr Asp Gly Ala Asp Tyr
130                 135                 140

Ile Ala Leu Asn Glu Asp Leu Arg Ser Trp Thr Ala Ala Asp Met Ala
145                 150                 155                 160

Ala Gln Ile Thr Lys Arg Lys Trp Glu Ala Ala Asp Glu Ala Glu Arg
                165                 170                 175

Arg Arg Ser Tyr Leu Gln Gly Leu Cys Val Glu Ser Leu Arg Arg Tyr
                180                 185                 190

Leu Glu Met Gly Lys Asp Thr Leu Gln Arg Ala Glu Pro Pro Lys Thr
                195                 200                 205

His Val Thr Arg His Pro Ser Ser Asp Leu Gly Val Thr Leu Arg Cys
            210                 215                 220

Trp Ala Leu Gly Phe Tyr Pro Lys Glu Ile Ser Leu Thr Trp Gln Arg
225                 230                 235                 240

Glu Gly Gln Asp Gln Ser Gln Asp Met Glu Leu Val Glu Thr Arg Pro
                245                 250                 255

Ser Gly Asp Gly Thr Phe Gln Lys Trp Ala Ala Leu Val Val Pro Pro
            260                 265                 270

Gly Glu Glu Gln Ser Tyr Thr Cys His Val Gln His Glu Gly Leu Gln
                275                 280                 285

Glu Pro Leu Thr Leu Arg Trp Asp Pro Ala Gln Pro Pro Val Pro Ile
        290                 295                 300

Val Gly Ile Ile Val Gly Leu Val Leu Val Leu Val Ala Gly Ala Met
305                 310                 315                 320

Val Ala Gly Val Val Ile Trp Arg Lys Thr Arg Ser Gly Glu Lys Gly
                325                 330                 335

Gly Ser Tyr Thr Gln Ala Ala Gly Ser Asp Ser Asp Gln Gly Ser Asp
            340                 345                 350

Val Ser Leu Thr Lys Asp Pro Arg Val
            355                 360

<210> SEQ ID NO 10
<211> LENGTH: 364
<212> TYPE: PRT
<213> ORGANISM: Sus scrofa

<400> SEQUENCE: 10

Met Arg Val Arg Gly Pro Gln Ala Ile Leu Ile Leu Leu Ser Gly Ala
 1               5                  10                  15

Leu Ala Leu Thr Gly Thr Arg Ala Gly Pro His Ser Leu Arg Tyr Phe
                20                  25                  30

Asp Thr Ala Val Ser Arg Pro Asp Arg Gly Asp Ser Arg Phe Leu Thr
         35                  40                  45
```

-continued

```
Val Gly Tyr Val Asp Asp Thr Gln Phe Val Arg Phe Asp Ser Asp Ala
         50                  55                  60
Pro Asn Pro Arg Glu Glu Pro Arg Ala Pro Trp Ile Gln Gln Glu Gly
 65                  70                  75                  80
Gln Asp Tyr Trp Asp Arg Glu Thr Gln Ile Ser Lys Glu Thr Ala Gln
             85                  90                  95
Thr Tyr Arg Val Asp Leu Asn Thr Leu Arg Ser Tyr Asn Gln Ser
            100                 105                 110
Glu Ala Gly Ser His Thr Leu Gln Ser Met Tyr Gly Cys Asp Val Gly
            115                 120                 125
Pro Asp Gly Leu Phe Leu Arg Gly Tyr Ser Gln Phe Gly Tyr Asp Gly
        130                 135                 140
Ala Asp Tyr Leu Ala Leu Asn Glu Asp Leu Arg Ser Trp Thr Ala Ala
145                 150                 155                 160
Asp Thr Ala Ala Gln Ile Ser Lys Arg Lys Phe Asp Ala Ala Asn Val
                165                 170                 175
Ala Glu Gln Glu Arg Ser Tyr Leu Gln Gly Leu Cys Val Glu Gly Leu
            180                 185                 190
Arg Arg Tyr Leu Glu Met Gly Lys Asp Thr Leu Gln Arg Ala Glu Pro
        195                 200                 205
Pro Lys Thr His Val Thr Arg His Pro Ser Ser Asp Leu Gly Val Thr
    210                 215                 220
Leu Arg Cys Trp Ala Leu Gly Phe Tyr Pro Lys Glu Ile Ser Leu Thr
225                 230                 235                 240
Trp Gln Arg Glu Gly Gln Asp Gln Ser Gln Asp Met Glu Leu Val Glu
                245                 250                 255
Thr Arg Pro Ser Gly Asp Gly Thr Phe Gln Lys Trp Ala Ala Leu Val
            260                 265                 270
Val Pro Pro Gly Glu Glu Gln Ser Tyr Thr Cys His Val Gln His Glu
        275                 280                 285
Gly Leu Gln Glu Pro Leu Thr Leu Arg Trp Glu Pro Pro Gln Pro Pro
    290                 295                 300
Val Pro Ile Val Gly Ile Phe Val Gly Leu Val Leu Val Leu Val Ala
305                 310                 315                 320
Gly Thr Met Val Thr Gly Val Val Ile Trp Arg Lys Lys Arg Ser Gly
                325                 330                 335
Glu Lys Gly Gly Ser Tyr Thr Gln Ala Ala Gly Ser Asp Ser Ala Gln
            340                 345                 350
Gly Ser Asp Val Ser Leu Thr Lys Asp Pro Arg Val
        355                 360

<210> SEQ ID NO 11
<211> LENGTH: 364
<212> TYPE: PRT
<213> ORGANISM: Sus scrofa

<400> SEQUENCE: 11

Met Arg Val Arg Gly Pro Gln Ala Ile Leu Ile Leu Leu Ser Gly Ala
 1               5                  10                  15
Leu Ala Leu Thr Gly Thr Arg Ala Gly Pro His Ser Leu Ser Tyr Phe
             20                  25                  30
Tyr Thr Ala Val Ser Arg Pro Asp Leu Gly Asp Ser Arg Phe Ile Ala
         35                  40                  45
Val Gly Tyr Val Asp Asp Thr Gln Phe Val Arg Phe Asp Ser Asp Ala
```

```
            50                  55                  60
Pro Asn Pro Arg Met Glu Pro Arg Ala Pro Trp Ile Glu Lys Glu Gly
 65                  70                  75                  80

Gln Glu Tyr Trp Asp Arg Glu Thr Gln Ile Gln Arg Asp Thr Ser Gln
                 85                  90                  95

Thr Tyr Arg Val Asp Leu Lys Thr Leu Arg Gly Tyr Tyr Asn Gln Ser
                100                 105                 110

Glu Ala Gly Ser His Thr Leu Gln Ser Met Tyr Gly Cys Tyr Leu Gly
                115                 120                 125

Pro Asp Gly Leu Leu Leu Arg Gly Tyr Arg Gln Phe Ala Tyr Asp Gly
            130                 135                 140

Ala Asp Tyr Leu Ala Leu Asn Glu Asp Leu Arg Ser Trp Thr Ala Ala
145                 150                 155                 160

Asp Met Ala Ala Gln Ile Ser Lys Arg Lys Trp Glu Ala Ala Asn Ala
                165                 170                 175

Ala Glu Gln Glu Arg Ser Tyr Leu Gln Gly Arg Cys Val Glu Trp Leu
                180                 185                 190

Arg Arg Tyr Leu Glu Met Gly Lys Asp Thr Leu Gln Arg Ala Glu Pro
            195                 200                 205

Pro Lys Thr His Val Thr Arg His Pro Ser Ser Asp Leu Gly Val Thr
            210                 215                 220

Leu Arg Cys Trp Ala Leu Gly Phe Tyr Pro Lys Glu Ile Ser Leu Thr
225                 230                 235                 240

Trp Gln Arg Glu Gly Gln Asp Gln Ser Gln Asp Met Glu Leu Val Glu
                245                 250                 255

Thr Arg Pro Ser Gly Asp Gly Thr Phe Gln Lys Trp Ala Ala Leu Val
            260                 265                 270

Val Pro Pro Gly Glu Glu Gln Ser Tyr Thr Cys His Val Gln His Glu
            275                 280                 285

Gly Leu Gln Glu Pro Leu Thr Leu Arg Trp Asp Pro Gln Pro Pro
290                 295                 300

Val Pro Ile Val Gly Ile Ile Val Gly Leu Val Leu Val Leu Val Ala
305                 310                 315                 320

Gly Ala Met Val Ala Gly Val Val Ile Trp Arg Lys Lys Arg Ser Gly
                325                 330                 335

Glu Lys Gly Gly Ser Tyr Thr Gln Ala Ala Gly Ser Asp Ser Ala Gln
            340                 345                 350

Gly Ser Asp Val Ser Leu Thr Lys Asp Pro Arg Val
            355                 360

<210> SEQ ID NO 12
<211> LENGTH: 364
<212> TYPE: PRT
<213> ORGANISM: Sus scrofa

<400> SEQUENCE: 12

Met Arg Val Arg Gly Pro Gln Ala Ile Leu Ile Leu Leu Ser Gly Ala
  1               5                  10                  15

Leu Ala Leu Thr Gly Thr Gln Ala Gly Pro His Ser Leu Arg Tyr Phe
                 20                  25                  30

Asp Thr Ala Val Ser Arg Pro Asp Arg Gly Glu Pro Arg Phe Ile Glu
                 35                  40                  45

Val Gly Tyr Val Asp Asp Thr Gln Phe Val Arg Phe Asp Ser Asp Ala
             50                  55                  60
```

```
Pro Asn Pro Arg Met Glu Pro Arg Ala Pro Trp Ile Gln Gln Glu Gly
 65                  70                  75                  80

Gln Glu Tyr Trp Asp Arg Asn Thr Arg Asn Ala Met Gly Asn Ala Gln
                 85                  90                  95

Ile Tyr Arg Gly Asn Leu Arg Thr Ala Leu Gly Tyr Tyr Asn Gln Ser
            100                 105                 110

Glu Ala Gly Ser His Thr Ile Gln Ile Met Tyr Gly Cys Asp Val Gly
        115                 120                 125

Pro Asp Gly Leu Leu Leu Arg Gly Tyr Ser Gln Asp Ala Tyr Asp Gly
130                 135                 140

Ala Asp Tyr Ile Ala Leu Asn Glu Asp Leu Arg Ser Trp Thr Ala Ala
145                 150                 155                 160

Asp Thr Ala Ala Gln Ile Thr Lys Arg Lys Trp Glu Ala Ala Asp Glu
                165                 170                 175

Ala Glu Arg Arg Arg Ser Tyr Leu Gln Gly Thr Cys Val Glu Trp Leu
            180                 185                 190

Gln Lys Tyr Leu Gln Met Gly Lys Asp Thr Leu Gln Arg Ala Glu Pro
        195                 200                 205

Pro Lys Thr His Val Thr Arg His Pro Ser Ser Asp Leu Gly Val Thr
210                 215                 220

Leu Arg Cys Trp Ala Leu Gly Phe Tyr Pro Lys Glu Ile Ser Leu Thr
225                 230                 235                 240

Trp Gln Arg Glu Gly Gln Asp Gln Ser Gln Asp Met Glu Leu Val Glu
                245                 250                 255

Thr Arg Pro Ser Gly Asp Gly Thr Phe Gln Lys Trp Ala Ala Leu Val
            260                 265                 270

Val Pro Pro Gly Glu Glu Gln Ser Tyr Thr Cys His Val Gln His Glu
        275                 280                 285

Gly Leu Gln Glu Pro Leu Thr Leu Arg Trp Asp Pro Pro Gln Pro Pro
290                 295                 300

Val Pro Ile Val Gly Ile Ile Val Gly Leu Val Leu Val Leu Val Ala
305                 310                 315                 320

Gly Ala Val Val Ala Gly Val Val Ile Trp Arg Lys Lys Arg Ser Gly
                325                 330                 335

Glu Lys Gly Gly Ser Tyr Thr Gln Ala Ala Gly Ser Asp Ser Ala Gln
            340                 345                 350

Gly Ser Asp Val Ser Leu Thr Lys Asp Pro Arg Val
        355                 360

<210> SEQ ID NO 13
<211> LENGTH: 34
<212> TYPE: DNA
<213> ORGANISM: Artificial
<220> FEATURE:
<223> OTHER INFORMATION: oligonucleotide for PCR

<400> SEQUENCE: 13
atcgaagctt atggggcctg agccctctct cctg                              34

<210> SEQ ID NO 14
<211> LENGTH: 44
<212> TYPE: DNA
<213> ORGANISM: Artificial
<220> FEATURE:
<223> OTHER INFORMATION: oligonucleotide for PCR

<400> SEQUENCE: 14
```

```
atcgaagctt atgcgggtca gaggccctca agccatcctc attc          44
```

<210> SEQ ID NO 15
<211> LENGTH: 39
<212> TYPE: DNA
<213> ORGANISM: Artificial
<220> FEATURE:
<223> OTHER INFORMATION: oligonucleotide for PCR

<400> SEQUENCE: 15

```
cgatctcgag tcacactcta ggatccttgg gtaagggac               39
```

<210> SEQ ID NO 16
<211> LENGTH: 14
<212> TYPE: PRT
<213> ORGANISM: Homo sapiens

<400> SEQUENCE: 16

Gln Tyr Ala Tyr Asp Gly Lys Asp Tyr Ile Ala Leu Asn Glu
 1               5                  10

<210> SEQ ID NO 17
<211> LENGTH: 14
<212> TYPE: PRT
<213> ORGANISM: Sus scrofa

<400> SEQUENCE: 17

Gln Asp Ala Tyr Asp Gly Ala Asp Tyr Ile Ala Leu Asn Glu
 1               5                  10

<210> SEQ ID NO 18
<211> LENGTH: 14
<212> TYPE: PRT
<213> ORGANISM: Sus scrofa

<400> SEQUENCE: 18

Gln Phe Gly Tyr Asp Gly Ala Asp Tyr Leu Ala Leu Asn Glu
 1               5                  10

<210> SEQ ID NO 19
<211> LENGTH: 14
<212> TYPE: PRT
<213> ORGANISM: Sus scrofa

<400> SEQUENCE: 19

Gln Phe Ala Tyr Asp Gly Ala Asp Tyr Leu Ala Leu Asn Glu
 1               5                  10

<210> SEQ ID NO 20
<211> LENGTH: 25
<212> TYPE: PRT
<213> ORGANISM: Homo sapiens

<400> SEQUENCE: 20

Asp Gln Thr Gln Asp Thr Glu Leu Val Glu Thr Arg Pro Ala Gly Asp
 1               5                  10                  15

Arg Thr Phe Gln Lys Trp Ala Ala Val
                20                  25

<210> SEQ ID NO 21
<211> LENGTH: 25
<212> TYPE: PRT
<213> ORGANISM: Sus scrofa

<400> SEQUENCE: 21

Asp Gln Ser Gln Asp Met Glu Leu Val Glu Thr Arg Pro Ser Gly Asp
1               5                   10                  15

Gly Thr Phe Gln Lys Trp Ala Ala Leu
            20              25

<210> SEQ ID NO 22
<211> LENGTH: 4
<212> TYPE: PRT
<213> ORGANISM: Homo sapiens

<400> SEQUENCE: 22

Asn Leu Arg Lys
1

<210> SEQ ID NO 23
<211> LENGTH: 4
<212> TYPE: PRT
<213> ORGANISM: Sus scrofa

<400> SEQUENCE: 23

Gly Leu Asn Thr
1

<210> SEQ ID NO 24
<211> LENGTH: 4
<212> TYPE: PRT
<213> ORGANISM: Sus scrofa

<400> SEQUENCE: 24

Asn Leu Lys Asn
1

<210> SEQ ID NO 25
<211> LENGTH: 4
<212> TYPE: PRT
<213> ORGANISM: Sus scrofa

<400> SEQUENCE: 25

Asn Leu Arg Thr
1

<210> SEQ ID NO 26
<211> LENGTH: 4
<212> TYPE: PRT
<213> ORGANISM: Sus scrofa

<400> SEQUENCE: 26

Asp Leu Asn Thr
1

<210> SEQ ID NO 27
<211> LENGTH: 4
<212> TYPE: PRT
<213> ORGANISM: Sus scrofa

<400> SEQUENCE: 27

Asp Leu Lys Thr
1

<210> SEQ ID NO 28
<211> LENGTH: 4
<212> TYPE: PRT
<213> ORGANISM: Homo sapiens

```
<400> SEQUENCE: 28

Ser Leu Arg Asn
 1

<210> SEQ ID NO 29
<211> LENGTH: 7
<212> TYPE: PRT
<213> ORGANISM: Homo sapiens

<400> SEQUENCE: 29

Asn Leu Arg Ile Ala Leu Arg
 1               5

<210> SEQ ID NO 30
<211> LENGTH: 7
<212> TYPE: PRT
<213> ORGANISM: Sus scrofa

<400> SEQUENCE: 30

Gly Leu Asn Thr Leu Arg Gly
 1               5

<210> SEQ ID NO 31
<211> LENGTH: 7
<212> TYPE: PRT
<213> ORGANISM: Sus scrofa

<400> SEQUENCE: 31

Asn Leu Lys Asn Leu Arg Gly
 1               5

<210> SEQ ID NO 32
<211> LENGTH: 7
<212> TYPE: PRT
<213> ORGANISM: Sus scrofa

<400> SEQUENCE: 32

Asn Leu Arg Thr Ala Leu Gly
 1               5

<210> SEQ ID NO 33
<211> LENGTH: 7
<212> TYPE: PRT
<213> ORGANISM: Sus scrofa

<400> SEQUENCE: 33

Asp Leu Asn Thr Leu Arg Ser
 1               5

<210> SEQ ID NO 34
<211> LENGTH: 7
<212> TYPE: PRT
<213> ORGANISM: Sus scrofa

<400> SEQUENCE: 34

Asp Leu Lys Thr Leu Arg Gly
 1               5

<210> SEQ ID NO 35
<211> LENGTH: 1086
<212> TYPE: DNA
<213> ORGANISM: Artificial
<220> FEATURE:
<221> NAME/KEY: consensus sequence
<221> NAME/KEY: misc_feature
```

```
<222> LOCATION: (126)...(126)
<223> OTHER INFORMATION: n = G,T or C
<221> NAME/KEY: misc_feature
<222> LOCATION: (261)...(261)
<223> OTHER INFORMATION: n = A,C or T
<221> NAME/KEY: misc_feature
<222> LOCATION: (272)...(272)
<223> OTHER INFORMATION: n = A,G or C
<221> NAME/KEY: misc_feature
<222> LOCATION: (490)...(490)
<223> OTHER INFORMATION: n = T,G or A
<221> NAME/KEY: misc_feature
<222> LOCATION: (551)...(551)
<223> OTHER INFORMATION: n = G,C or T
<221> NAME/KEY: misc_feature
<222> LOCATION: (939)...(939)
<223> OTHER INFORMATION: n = T,C or G

<400> SEQUENCE: 35
atggggcctg gagccctctt cctgctgctg tcggggaccc tggccctgac cgggacccag      60
gcgggtcccc actccctgag ctatttctac accgccgtgt cccggcccga ccgcggggag     120
ccccgnttca tcgccgtcgg ctacgtggac gacacgcagt tcgtgcggtt cgacaactac     180
gccccgaatc cgcggatgga gcctcggtg ccgtggatac agcaggaggg gcaggactat      240
tgggatgagg agacgcggaa ngtcaaggac ancgcacaga cttccgagt gggcctgaac       300
accctgcgcg gctactacaa ccagagcgag gccgggtctc acaccctcca gagcatgtac     360
ggctgctact tgggaccaga cgggctcctc ctccacgggt acagacagga cgcctacgac     420
ggcgccgatt acatcgccct gaacgaggac ctgcgctcct ggaccgcggc ggacatggcg     480
gctcagatcn ccaagcgcaa gtgggaggcg gccgatgagg cggagcggag gaggagctac     540
ctgcagggcc ngtgtgtgga gtggctccgc agatacctgg agatggggaa ggacacgctg     600
cagcgcgcag agcctccaaa gacacatgtg acccgccacc ccagctctga cctggggtc      660
accttgaggt gctgggccct gggcttctac cctaaggaga tctccctgac ctggcagcgg     720
gagggccagg accagagcca ggacatggag ctggtggaga ccaggccctc aggggatggg     780
accttccaga agtgggcggc cctggtggtg cctcctggag aggagcagag ctacacctgc     840
catgtgcagc acgagggcct gcaggagccc ctcacccctga atgggaccc tgctcagccc     900
cccgtcccca tcgtgggcat cattgttggc ctggttctng tcctggtcgc tggagccatg     960
gtggctggag ttgtgatctg gaggaagacg cgctcaggtg aaaaggagg gagctacact     1020
caggctgcag gcagtgacag tgcccagggc tccgatgtgt cccttaccaa ggatcctaga     1080
gtgtga                                                                1086

<210> SEQ ID NO 36
<211> LENGTH: 1095
<212> TYPE: DNA
<213> ORGANISM: Artificial
<220> FEATURE:
<221> NAME/KEY: consensus sequence
<221> NAME/KEY: misc_feature
<222> LOCATION: (271)...(271)
<223> OTHER INFORMATION: n = A,C or G
<221> NAME/KEY: misc_feature
<222> LOCATION: (272)...(272)
<223> OTHER INFORMATION: n = G,A or C
<221> NAME/KEY: misc_feature
<222> LOCATION: (275)...(275)
<223> OTHER INFORMATION: n = A,G or T
<221> NAME/KEY: misc_feature
<222> LOCATION: (527)...(527)
<223> OTHER INFORMATION: n = T,C or A
<221> NAME/KEY: misc_feature
<222> LOCATION: (560)...(560)
```

-continued

<223> OTHER INFORMATION: n = T,G or C

<400> SEQUENCE: 36

| | |
|---|---|
| atgcgggtca gaggccctca agccatcctc attctgctgt cgggggccct ggccctgacc | 60 |
| gggacccggg cgggtcccca ctccctgagg tatttcgaca ccgccgtgtc ccggcccgac | 120 |
| cgcggggact cccgcttcat cgccgtcggc tacgtggacg acacgcagtt cgtgaggttc | 180 |
| gacagcgacg ccccgaatcc gcggatggag ccgcgggcgc cgtggataca gcaggagggg | 240 |
| caggagtatt gggatcggga gacacagatc nncanggaca ccgcacagac ttaccgagtg | 300 |
| gacctgaaca ccctgcgcgg ctactacaac cagagcgagg ccgggtctca caccctccag | 360 |
| agcatgtacg gctgcgacgt gggaccagac gggctcctcc tccgcgggta cagtcagttc | 420 |
| gcctacgacg gcgccgatta cctcgccctg aacgaggacc tgcgctcctg gaccgcggcg | 480 |
| gacacggcgg ctcagatctc caagcgcaag tgggaggcgg ccaatgnggc ggagcaggag | 540 |
| aggagctacc tgcagggccn gtgtgtggag tggctccgca gatacctgga gatggggaag | 600 |
| gacacgctgc agcgcgcaga gcctccaaag acacatgtga cccgccaccc cagctctgac | 660 |
| ctggggtca ccttgaggtg ctgggccctg gcttctacc taaggagat ctccctgacc | 720 |
| tggcagcggg agggccagga ccagagccag gacatggagc tggtggagac caggccctca | 780 |
| ggggatggga ccttccagaa gtgggcggcc ctggtggtgc ctcctggaga ggagcagagc | 840 |
| tacacctgcc atgtgcagca cgagggcctg caggagcccc tcaccctgag atgggaccct | 900 |
| cctcagcccc ccgtccccat cgtgggcatc attgttggca tggttctcgt cctggtcgct | 960 |
| ggagccatgg tggctggagt tgtgatctgg aggaagaagc gctcaggtga aaaggaggg | 1020 |
| agctacactc aggctgcagg cagtgacagt gcccagggct ccgatgtgtc ccttaccaag | 1080 |
| gatcctagag tgtga | 1095 |

<210> SEQ ID NO 37
<211> LENGTH: 363
<212> TYPE: PRT
<213> ORGANISM: Artificial
<220> FEATURE:
<221> NAME/KEY: consensus sequence

<400> SEQUENCE: 37

Met Arg Val Gly Pro Gly Ala Leu Leu Leu Leu Ser Gly Ala Leu
1               5                   10                  15

Ala Leu Thr Gly Thr Gln Ala Gly Pro His Ser Leu Ser Tyr Phe Asp
            20                  25                  30

Thr Ala Val Ser Arg Pro Asp Arg Gly Asp Ser Arg Phe Ile Ala Val
        35                  40                  45

Gly Tyr Val Asp Asp Thr Gln Phe Val Arg Phe Asp Ser Asp Ala Pro
    50                  55                  60

Asn Pro Arg Met Glu Pro Arg Ala Pro Trp Ile Gln Gln Glu Gly Gln
65                  70                  75                  80

Glu Tyr Trp Asp Arg Glu Thr Gln Asn Ala Lys Gly Thr Ala Gln Thr
                85                  90                  95

Tyr Arg Val Gly Leu Asn Thr Leu Arg Gly Tyr Tyr Asn Gln Ser Glu
            100                 105                 110

Ala Gly Ser His Thr Leu Gln Ser Met Tyr Gly Cys Asp Val Gly Pro
        115                 120                 125

Asp Gly Leu Leu Leu Arg Gly Tyr Arg Gln Asp Ala Tyr Asp Gly Ala
    130                 135                 140

-continued

```
Asp Tyr Ile Ala Leu Asn Glu Asp Leu Arg Ser Trp Thr Ala Ala Asp
145                 150                 155                 160

Thr Ala Ala Gln Ile Ser Lys Arg Lys Trp Glu Ala Ala Asp Glu Ala
                165                 170                 175

Glu Gln Glu Arg Ser Tyr Leu Gln Gly Leu Cys Val Glu Trp Leu Arg
            180                 185                 190

Arg Tyr Leu Glu Met Gly Lys Asp Thr Leu Gln Arg Ala Glu Pro Pro
        195                 200                 205

Lys Thr His Val Thr Arg His Pro Ser Ser Asp Leu Gly Val Thr Leu
    210                 215                 220

Arg Cys Trp Ala Leu Gly Phe Tyr Pro Lys Glu Ile Ser Leu Thr Trp
225                 230                 235                 240

Gln Arg Glu Gly Gln Asp Gln Ser Gln Asp Met Glu Leu Val Glu Thr
                245                 250                 255

Arg Pro Ser Gly Asp Gly Thr Phe Gln Lys Trp Ala Ala Leu Val Val
            260                 265                 270

Pro Pro Gly Glu Glu Gln Ser Tyr Thr Cys His Val Gln His Glu Gly
        275                 280                 285

Leu Gln Glu Pro Leu Thr Leu Arg Trp Asp Pro Pro Gln Pro Pro Val
    290                 295                 300

Pro Ile Val Gly Ile Ile Val Gly Leu Val Leu Val Leu Val Ala Gly
305                 310                 315                 320

Ala Met Val Ala Gly Val Val Ile Trp Arg Lys Lys Arg Ser Gly Glu
                325                 330                 335

Lys Gly Gly Ser Tyr Thr Gln Ala Ala Gly Ser Asp Ser Ala Gln Gly
            340                 345                 350

Ser Asp Val Ser Leu Thr Lys Asp Pro Arg Val
        355                 360
```